United States Patent
Okino et al.

(10) Patent No.: US 10,683,551 B2
(45) Date of Patent: Jun. 16, 2020

(54) DETECTING METHYLATION IN A SUBPOPULATION OF GENOMIC DNA

(71) Applicant: Bio-Rad Laboratories, Inc., Hercules, CA (US)

(72) Inventors: Steven T. Okino, San Carlos, CA (US); Yan Wang, San Francisco, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 15/411,855

(22) Filed: Jan. 20, 2017

(65) Prior Publication Data

US 2017/0159132 A1 Jun. 8, 2017

Related U.S. Application Data

(63) Continuation of application No. 13/396,496, filed on Feb. 14, 2012, now abandoned.

(60) Provisional application No. 61/442,918, filed on Feb. 15, 2011.

(51) Int. Cl.
*C12Q 1/68* (2018.01)
*C12Q 1/6886* (2018.01)
*C12Q 1/6806* (2018.01)
*C12Q 1/6809* (2018.01)
*C12Q 1/6804* (2018.01)

(52) U.S. Cl.
CPC ......... *C12Q 1/6886* (2013.01); *C12Q 1/6804* (2013.01); *C12Q 1/6806* (2013.01); *C12Q 1/6809* (2013.01); *C12Q 2600/154* (2013.01); *C12Q 2600/158* (2013.01)

(58) Field of Classification Search
USPC ......... 435/6.1, 6.11, 91.1, 183; 436/94, 501; 536/23.1, 24.3, 24.33
See application file for complete search history.

(56) References Cited

U.S. PATENT DOCUMENTS

| | | |
|---|---|---|
| 5,128,247 A | 7/1992 | Koller |
| 5,459,055 A | 10/1995 | Jendrisak et al. |
| 5,972,608 A | 10/1999 | Peterson et al. |
| 6,331,393 B1 | 12/2001 | Laird et al. |
| 6,492,168 B1 | 12/2002 | Kladde et al. |
| 8,652,821 B2 | 2/2014 | Okino et al. |
| 8,728,987 B2 | 5/2014 | Kong et al. |
| 9,273,347 B2 | 3/2016 | Okino |

(Continued)

FOREIGN PATENT DOCUMENTS

| | | |
|---|---|---|
| EP | 2 614 160 B1 | 4/2016 |
| EP | 2675913 | 12/2016 |

(Continued)

OTHER PUBLICATIONS

Chimonidou et al., DNA Methylation of Tumor Suppressor and Metastasis Suppressor Genes in Circulating Tumor Cell. Clinical Chemistry, 57, 1169-1177, 2011.*

(Continued)

*Primary Examiner* — Frank W Lu
(74) *Attorney, Agent, or Firm* — Emily M. Haliday; Weaver Austin Villeneuve & Sampson LLP

(57) ABSTRACT

This invention provides methods of determining the biological, pathological, genetic, epigenetic or disease status in a biological sample by determining the methylation status of a subpopulation of genomic DNA in the sample.

9 Claims, 3 Drawing Sheets

(56) References Cited

U.S. PATENT DOCUMENTS

| | | |
|---|---|---|
| 9,752,177 B2 | 9/2017 | Kong et al. |
| 2002/0065609 A1 | 5/2002 | Ashby |
| 2002/0119455 A1 | 8/2002 | Chan |
| 2002/0177139 A1 | 11/2002 | Greenfield et al. |
| 2003/0077609 A1 | 4/2003 | Jacobsen et al. |
| 2003/0176438 A1 | 9/2003 | Arienti et al. |
| 2004/0014086 A1 | 1/2004 | Stamatoyannapoulos et al. |
| 2004/0023206 A1 | 2/2004 | Polansky |
| 2004/0023207 A1 | 2/2004 | Polansky |
| 2005/0079516 A1 | 4/2005 | Maniotis et al. |
| 2006/0166206 A1 | 7/2006 | Urnov et al. |
| 2006/0286570 A1 | 12/2006 | Rowlen et al. |
| 2007/0009937 A1 | 1/2007 | Laemmli et al. |
| 2007/0009954 A1 | 1/2007 | Wang et al. |
| 2007/0020716 A1 | 1/2007 | Lerman et al. |
| 2007/0031829 A1 | 2/2007 | Yasuno et al. |
| 2007/0042400 A1 | 2/2007 | Choi et al. |
| 2007/0042419 A1 | 2/2007 | Barany et al. |
| 2007/0072218 A1 | 3/2007 | Liang et al. |
| 2009/0061415 A1 | 3/2009 | Ebersole et al. |
| 2009/0130237 A1 | 5/2009 | Cohen |
| 2009/0148891 A1 | 6/2009 | Bauer et al. |
| 2009/0155791 A1 | 6/2009 | Wojdacz et al. |
| 2009/0215066 A1 | 8/2009 | Ahmed et al. |
| 2009/0286304 A1 | 11/2009 | Latham et al. |
| 2010/0136559 A1 | 6/2010 | Okino et al. |
| 2011/0195486 A1 | 8/2011 | Liu et al. |
| 2011/0306042 A1 | 12/2011 | Jouvenot |
| 2012/0014977 A1 | 1/2012 | Furihata et al. |
| 2012/0064517 A1 | 3/2012 | Okino |
| 2012/0070829 A1 | 3/2012 | Okino et al. |
| 2012/0082991 A1 | 4/2012 | Okino |
| 2012/0100597 A1 | 4/2012 | Okino et al. |
| 2012/0165219 A1 | 6/2012 | Van Der Zaag et al. |
| 2012/0208193 A1 | 8/2012 | Okino et al. |
| 2012/0231972 A1 | 9/2012 | Golyshin et al. |
| 2012/0252012 A1 | 10/2012 | Armougom et al. |
| 2012/0253689 A1 | 10/2012 | Rogan |
| 2012/0322058 A1 | 12/2012 | Regan et al. |
| 2013/0035239 A1 | 2/2013 | Kong et al. |
| 2013/0109737 A1 | 5/2013 | Young et al. |
| 2013/0225623 A1 | 8/2013 | Buxbaum et al. |
| 2014/0220586 A1 | 8/2014 | Kong et al. |
| 2016/0186258 A1 | 6/2016 | Okino |
| 2016/0208312 A9 | 7/2016 | Kong et al. |
| 2016/0273027 A1 | 9/2016 | Okino et al. |
| 2017/0218444 A1 | 8/2017 | Okino et al. |

FOREIGN PATENT DOCUMENTS

| | | |
|---|---|---|
| FR | 2792000 A1 | 10/2000 |
| JP | 2002-209588 A | 7/2002 |
| JP | 5871933 B2 | 1/2016 |
| JP | 5917519 B2 | 4/2016 |
| WO | WO 00/29618 | 5/2000 |
| WO | WO 02/097135 | 12/2002 |
| WO | WO 03/004702 | 1/2003 |
| WO | WO 03/035894 | 5/2003 |
| WO | WO 2003/076949 | 9/2003 |
| WO | WO 2006/096727 | 9/2006 |
| WO | WO 2009/061840 | 5/2009 |
| WO | WO 2010/065266 | 6/2010 |
| WO | WO 2011/005221 | 1/2011 |
| WO | WO 2012/034007 | 3/2012 |
| WO | WO 2012/034013 | 3/2012 |
| WO | WO 2012/034041 | 3/2012 |
| WO | WO 2012/054613 | 4/2012 |
| WO | WO 2012/112606 | 8/2012 |
| WO | WO 2012/129436 | 9/2012 |
| WO | WO 2013/019960 | 2/2013 |
| WO | WO 2014/146025 | 9/2014 |
| WO | WO 2015/080966 | 6/2015 |

OTHER PUBLICATIONS

Mikeska et al., DNA methylation biomarkers in cancer: progress towards clinical implementation. Expert Rev. Mol. Diagn. 12, 473-487, 2012.*
Waki et al., Age-related methylation of tumor suppressor and tumor-related genes: an analysis of autopsy samples. Oncogene, 22, 4128-4133, 2003.*
"DNA methylation" from Wikipedia, the free encyclopedia. Printed on May 29, 2018.*
U.S. Appl. No. 15/427,845, dated Feb. 8, 2017, Okino et al.
U.S. Office Action dated May 31, 2013 issued in U.S. Appl. No. 13/396,496.
U.S. Final Office Action dated Dec. 5, 2013 issued in U.S. Appl. No. 13/396,496.
U.S. Office Action dated Sep. 26, 2014 issued in U.S. Appl. No. 13/396,496.
U.S. Final Office Action dated May 18, 2015 issued in U.S. Appl. No. 13/396,496.
U.S. Office Action dated Jan. 15, 2016 issued in U.S. Appl. No. 13/396,496.
U.S. Final Office Action dated Aug. 23, 2016 issued in U.S. Appl. No. 13/396,496.
U.S. Office Action dated Feb. 13, 2015 issued in U.S. Appl. No. 13/229,111.
U.S. Notice of Allowance dated Aug. 4, 2015 issued in U.S. Appl. No. 13/229,111.
U.S. Notice of Allowance dated Oct. 29, 2015 issued in U.S. Appl. No. 13/229,111.
U.S. Restriction Requirement dated Jan. 24, 2013 issued in U.S. Appl. No. 13/276,553.
U.S. Office Action dated Apr. 8, 2013 issued in U.S. Appl. No. 13/276,553.
U.S. Notice of Allowance dated Oct. 8, 2013 issued in U.S. Appl. No. 13/276,553.
U.S. Office Action dated Apr. 19, 2012 issued in U.S. Appl. No. 13/229,132.
U.S. Final Office Action dated Sep. 20, 2012 issued in U.S. Appl. No. 13/229,132.
U.S. Office Action dated Aug. 29, 2013 issued in U.S. Appl. No. 13/229,132.
U.S. Final Office Action dated Feb. 5, 2014 issued in U.S. Appl. No. 13/229,132.
U.S. Office Action dated Sep. 26, 2014 issued in U.S. Appl. No. 13/229,132.
U.S. Final Office Action dated Feb. 10, 2015 issued in U.S. Appl. No. 13/229,132.
U.S. Office Action dated Jul. 1, 2015 issued in U.S. Appl. No. 13/229,132.
U.S. Final Office Action dated Nov. 30, 2015 issued in U.S. Appl. No. 13/229,132.
U.S. Office Action dated Aug. 10, 2016 issued in U.S. Appl. No. 13/229,132.
U.S. Office Action dated May 24, 2013 issued in U.S. Appl. No. 13/565,464.
U.S. Final Office Action dated Jan. 9, 2014 issued in U.S. Appl. No. 13/565,464.
U.S. Notice of Allowance dated Mar. 17, 2014 issued in U.S. Appl. No. 13/565,464.
U.S. Office Action dated Jun. 16, 2016 issued in U.S. Appl. No. 14/256,861.
U.S. Final Office Action dated Nov. 14, 2016 issued in U.S. Appl. No. 14/256,861.
U.S. Notice of Allowance dated Jan. 23, 2017 issued in U.S. Appl. No. 14/256,861.
PCT International Search Report and Written Opinion, dated May 2, 2012, issued in PCT/US2012/025120.
PCT International Preliminary Report on Patentability, dated Aug. 29, 2013, issued in PCT/US2012/025120.

(56) References Cited

OTHER PUBLICATIONS

PCT International Search Report, dated Mar. 26, 2012, issued in PCT/US2011/050992.
PCT International Preliminary Report on Patentability, dated Mar. 21, 2013, issued in PCT/US2011/050992.
PCT International Search Report and Written Opinion, dated Feb. 22, 2012, issued in PCT/US2011/056900 [65654-819597].
PCT International Preliminary Report on Patentability, dated May 2, 2013, issued in PCT/US2011/056900 [65654-819597].
PCT International Search Report, dated Mar. 26, 2012, issued in PCT/US2011/050981.
PCT International Preliminary Report on Patentability and Written Opinion, dated Mar. 21, 2013, issued in PCT/US2011/050981.
PCT International Search Report, dated Oct. 22, 2012, issued in PCT/US2012/049344.
PCT International Preliminary Report on Patentability and Written Opinion, dated Feb. 13, 2014, issued in PCT/US2012/049344.
PCT International Search Report and Written Opinion, dated Feb. 25, 2015, issued in PCT/US2014/066822.
PCT International Preliminary Report on Patentability, dated Jun. 9, 2016, issued in PCT/US2014/066822.
Chinese First Office Action, dated Dec. 8, 2014, issued in Application No. CN 201280038451.3.
Chinese Second Office Action, dated Jun. 24, 2015, issued in Application No. CN 201280038451.3.
Chinese Decision of Rejection, dated Feb. 2, 2016, issued in Application No. CN 201280038451.3.
Chinese Office Action [The Details of the Reexamination Notification], dated Sep. 2, 2016, issued in Application No. CN 201280038451.3.
European Search Report, dated Dec. 17, 2014, issued in Application No. EP 12 705 595.2.
European Office Action dated Feb. 2, 2016 issued in Application No. EP 12 705 595.2.
Communication about Intention to Grant a European patent dated Jul. 21, 2016 issued in Application No. EP 12 705 595.2.
Decision to Grant a European patent dated Nov. 17, 2016 issued in Application No. EP 12 705 595.2.
European Extended European Search Report dated Dec. 20, 2013 issued in Application No. EP 11 824 173.6 .
Communication about Intention to Grant a European patent dated Oct. 6, 2015 issued in Application No. EP 11 824 173.6.
Decision to Grant a European patent dated Mar. 10, 2016 issued in Application No. EP 11 824 173.6.
European Office Action dated Sep. 11, 2014 issued in Application No. EP 11 824 173.6.
European Extended Search Report dated Feb. 20, 2014 issued in Application No. EP 11 824 170.2.
European Office Action dated Feb. 12, 2016 issued in Application No. EP 11 824 170.2.
European Extended European Search Report dated Feb. 5, 2015 issued in Application No. EP 12 819 299.4.
European Office Action dated Apr. 7, 2016 issued in Application No. EP 12 819 299.4.
Communication about Intention to Grant a European patent dated Feb. 6, 2017 issued in Application No. EP 12 819 299.4.
Japanese Office Action (Notice of Reasons for Rejection) dated Sep. 7, 2015 issued in Application No. JP 2013-528327.
Japanese Office Action dated Jul. 6, 2015 issued in Application No. JP 2013-528325.
Almeida, (Jan. 6, 2009) "Polymorphisms and DNA methylation of gene TP53 associated with extraaxial brain tumors," *Genet Mol Res.*, 8(1):8-18 (abstract only), 2 pages.
Antequera et al., (Aug. 10, 1990) "High levels of De Novo methylation and altered chromatin structure at CpG islands in cell lines," *Cell.* 62(3):503-514.
Arnold et al., (1996) "Thermal unfolding and proteolytic susceptibility of ribonuclease A," *Eur. J. Biochem.*, 237:862-869.

ARUP Laboratories, (Jan. 2012) "Septin 9 (SEPT9) Methylated DNA Detection by Real-Time PCR," *National Reference Laboratory*, 2 pages.
Barski, (May 2010) "Hypermethylation and transcriptional downregulation of the TIMP3 gene is associated with allelic loss on 22q12.3 and malignancy in meningiomas," *Brain Pathol.*20(3):623-31 (abstract only), 2 pages.
Barton, (Jan. 5, 2010) "Collagen and calcium-binding EGF domains 1 is frequently inactivated in ovarian cancer by aberrant promoter hypermethylation and modulates cell migration and survival," *Br J Cancer.*102(1):87-96 (abstract only), 2 pages.
Bennett, (Apr. 2010) "HPV status-independent association of alcohol and tobacco exposure or prior radiation therapy with promoter methylation of FUSSEL18, EBF3, IRX1, and SEPT9, but not SLC5A8, in head and neck squamous cell carcinomas," *Genes Chromosomes Cancer*,49(4):319-26 (abstract only), 2 pages.
Berdasco, (Dec. 22, 2009) "Epigenetic inactivation of the Sotos overgrowth syndrome gene histone methyltransferase NSD1 in human neuroblastoma and glioma," *Proc Natl Acad Sci USA* 106(51):21830-5 (abstract only), 2 pages.
Boyle et al., (Jan. 25, 2008) "High-Resolution Mapping and Characterization of Open Chromatin across the Genome," *CELL* 132:311-322.
Bryan, (Nov. 13, 2009) "Hypermethylation of the DLC1 CpG island does not alter gene expression in canine lymphoma," *BMC Genet.* ,10:73 (abstract only), 2 pages.
Buryanov et al., (2005) "The use of prokaryotic DNA methyltransferases as experimental and analytical tools in modern biology," *Analytical Biochemistry*, Academic Press Inc., New York, 338:1-11.
Carthew et al., (Feb. 20, 2009) "Origins and Mechanisms of miRNAs and siRNAs," *Cell*, 136(4):642-655.
Chen et al., (Nov. 2001) "Nucleosomes Are Translationally Positioned on the Active Allele and Rotationally Positioned on the Inactive Allele of the *HPRT* Promoter," *Molecular and Cellular Biology*, 21(22):7682-7695.
Chen, (Oct. 22, 2009) "Loss of prostasin (PRSS8) in human bladder transitional cell carcinoma cell lines is associated with epithelial-mesenchymal transition (EMT)," *BMC Cancer*, 9:377 (abstract only), 2 pages.
Cheng, (Feb. 2010) "Reduced CRYL1 expression in hepatocellular carcinoma confers cell growth advantages and correlates with adverse patient prognosis," *J Pathol.*,220(3):348-60 (abstract only), 2 pages.
Chim, (Dec. 2008) "Gene hypermethylation in multiple myeloma: lessons from a cancer pathway approach," *Clin Lymphoma Myeloma.*, 8(6):331-9 (abstract only), 2 pages.
Clarke et al., (Apr. 2009) "Continuous base identification for single-molecule nanopore DNA sequencing," *Nature Nanotechnology*, 4:265-270.
Crawford et al., (Jan. 27, 2004) "Identifying gene regulatory elements by genome-wide recovery of DNase hypersensitive sites," *Proc Natl Acad Sci USA*, 101(4):992-997.
Crawford et al., (Jul. 2006) "Dnase-chip: a high-resolution method to identify Dnase I hypersensitive sites using tiled microarrays," *Nat Methods.*, 3(7):503-509.
Crawford et al., (2006) "Genome-wide mapping of Dnase hypersensitive sites using massively parallel signature sequencing (MPSS)," *Genome Research*, 16:123-131.
Darzynkiewicz et al., (Jun. 1992) "Features of Apoptotic Cells Measured by Flow Cytometry," *Cytometry*, 13(8):795-808.
Dingwall et al., (1981) "High sequence specificity of micrococcal nuclease," *Nucleic Acids Research* 9(12):2659-2673.
Djeliova et al., (Jan. 1, 2002) "DNase 1 Sensitive Site in the Core Region of the Human β-globin Origin of Replication," *Journal of Cellular Biochemistry*, 87(3):279-283.
Drouin et al., (Jan. 2009) "Chapitre de livre: In vivo DNA analysis (anglais)," *Methods Mol Biol*, 148:175-219.
Eberhart et al., (1996) "Nuclease Sensitivity of Permeabilized Cells Confirms Altered Chromatin Formation at the Fragile X Locus," *Somatic Cell and Molecular Genetics*, 22(6):435-441.
Eid et al., (Jan. 2, 2009) "Real-Time DNA Sequencing from Single Polymerase Molecules," *Science*, 323:133-138.

(56) References Cited

OTHER PUBLICATIONS

"Epigenetic Regulation," *Innovative & Quality Tools for Epigenetics Research and DNA/RNA Purification*, The Epigenetics Company, Printed on Aug. 17, 2016, 3pp.
Epigenomics 2009 "The Septin 9 test—A simple blood-based test for early detection of colorectal cancer," p. 1-4.
Eurofins. LightCycler Probes for FRET Assays [online] Aug. 29, 2013 [retrieved Jan. 28, 2015]. Available on the internet<https://web.archive.org/web/20130829020418/http://www.eurofinsgenomics.eu/en/dna-ma-oligonucleotides/optimised-application-oligos/qper-probes/lightcycler-probes.aspx>, 1 page.
Fackler et al., (2003) "DNA Methylation of *RASSF1A, HIN-1, RAR-β, CYCLIN D2* and *Twist* in *In Situ* and Invasive Lobular Breast Carcinoma," *Int. J. Cancer*: 107:970-975.
Fackler, (Jun. 1, 2009) "Hypermethylated genes as biomarkers of cancer in women with pathologic nipple discharge," *Clin Cancer Res.*, 15(11):3802-11 (abstract only), 2 pages.
Fatemi et al., (2005) "Footprinting of mammalian promoters: use of a CpG DNA methyltransferase revealing nucleosome positions at a single molecule level," *Nucleic Acids Research*, 33(20):e176, pp. 1-9.
Ferrai et al., (Apr. 27, 2007) A Transcription-dependent Micrococcal Nuclease-resistant Fragment of the Urokinase-type Plasminogen Activator Promoter Interacts with the Enhancer, *The Journal of Biological Chemistry*, 282(17):12537-12546.
Flusberg et al., (Jun. 2010) "Direct detection of DNA methylation during single-molecule, real-time sequencing," *Nature Methods*, 7(6):461-465.
Foltz, (Jul. 23, 2009) "DNA methyltransferase-mediated transcriptional silencing in malignant glioma: a combined whole-genome microarray and promoter array analysis," *Oncogene*, 28(29): 2667-77 (abstract only), 2 pages.
Fu, (Nov. 2009) "Hypermethylation of APC promoter 1A is associated with moderate activation of Wnt signalling pathway in a subset of colorectal serrated adenomas," *Histopathology*,55(5):554-63 (abstract only), 2 pages.
Genomic imprinting from Wikipedia, the free encyclopedia. Printed on May 24, 2013, [Retrieved at http://en.wikipedia.org/wiki/Genomic imprinting on May 24, 2013], 10 pages.
Götze et al., (Dec. 17, 2009) "ECRG4 is a candidate tumor suppressor gene frequently hypermethylated in colorectal carcinoma and glioma," *BMC Cancer*, 9:447 (abstract only), 2 pages.
Grau et al., (Mar. 2011) "Hypermethylation of apoptotic genes as independent prognostic factor in neuroblastoma disease," *Mol Carcinog.*, 50(3):153-62 (abstract only), 2 pages.
Guldberg et al., (Jun. 2002) "Profiling DNA methylation by melting analysis," *Methods* 27(2):121-127, Abstract, 1 page.
Hagége et al. (2007) "Quantitative analysis of chromosome conformation capture assays (3C-qPCR)," *Nature Protocols* 2(7):1722-1733.
Hajkova et al., (2002) "DNA-Methylation Analysis by the Bisulfite-Assisted Genomic Sequencing Method," *Methods in Molecular Biology, DNA Methylation Protocols*, 200:143-1540.
Hamilton et al., (Dec. 15, 2009) "ATM regulates a RASSF1A-dependent DNA damage response," *Curr Biol.* 19(23):2020-5 (abstract only), 2 pages.
Hernandez-Munain, C. et al., (Jun. 1998) "Cooperation among Multiple Transcription Factors is Required for Access to Minimal T-Cell Receptor α-Enhancer Chromatin In Vivo," *Mol. and Cell. Biology*, 18(6):3223-3233.
"Heterochromatin, from Chromosome to Protein," *Atlas of Genetics and Cytogenetics in Oncology and Haematology*, Indexed on Aug. 9, 2016, Printed on Aug. 17, 2016, 14pp.
Huang et al., (Jan. 2010) "Genetic and epigenetic silencing of SCARA5 may contribute to human hepatocellular carcinoma by activating FAK signaling," *J Clin Invest.*, 120(1):223-41 (abstract only), 2 pages.
Hughes et al., (2000) "Widespread aneuploidy revealed by DNA microarray expression profiling," *Nature Genetics*, 25:333-337.

Ignatov et al. (Feb. 2010) "APC promoter hypermethylation is an early event in endometrial tumorigenesis," *Cancer Sci.*, 101(2):321-7 (abstract only), 2 pages.
Indovina et al. (Apr. 2010) "Downregulation and aberrant promoter methylation of p16INK4A: a possible novel heritable susceptibility marker to retinoblastoma," *J Cell Physiol.*, 223(1): 143-50 (abstract only), 2 pages.
Isomoto, (2009) "Epigenetic alterations in cholangiocarcinoma-sustained IL-6/STA T3 signaling in cholangio- carcinoma due to SOCS3 epigenetic silencing," *Digestion*, 79: Suppl 1:2-8 (abstract only), 2 pages.
Jacinto et al., (Jan. 2008) "Methyl-DNA immunoprecipitation (MeDIP): Hunting down the DNA methylome," *Biotechniques*, 44(1):35, 37, 39 passim, 5 pages.
Jessen et al., (2004) "Mapping chromatin structure in vivo using DNA methyltransferases," *Methods* 33:68-80.
Jha et al., (2010) "Reversal of hypermethylation and reactivation of the RAR~2 gene by natural compounds in cervical cancer cell lines," *Folia Biol* (Praha), 56(5):195-200 (abstract only), 1 page.
Jones et al., (Jun. 2002) "The fundamental role of epigenetic events in cancer," *Nat Rev Genet.* 3(6):415-28.
Kanduri, (Jan. 14, 2010) "Differential genome-wide array-based methylation profiles in prognostic subsets of chronic lymphocytic leukemia," *Blood* 115(2):296-305 (abstract only), 2 pages.
Kang et al., (Jun. 2003) "Role of the Promoter in Maintaining Transcriptionally Active Chromatin Structure and DNA Methylation Patterns In Vivo," *Molecular and Cellular Biology* 23(12):4150-4161.
Katsnelson, (May 2010) "Genomics goes beyond DNA sequence," *Nature*, 465:145.
Kauffmann et al., (2009) "Improvement of RNA secondary structure prediction using RNase H cleavage and randomized oligonucleotides," *Nucleic Acids Res.*, 37(18):e121, 11 pages.
Kim et al., (Dec. 2009) "Borderline and malignant phyllodes tumors display similar promoter methylation profiles," *Virchows Arch.*, 455(6):469-75 (abstract only), 2 pages.
Kitzis et al., (1980) "Localization of Phosphoproteins and of Protein Kinases in Chromatin from Hepatoma Tissue-Cultured Cells," *Eur J Biochem*, 111(1):237-244.
Kladde et al., (Feb. 1994) "Positioned nucleosomes Inhibit Dam methylation *in vivo*," *PNAS (USA)* 91(4)1361-1365.
Ko et al., (Jan. 1996) "Dioxin-induced *CYP1A1* Transcription In Vivo: the Aromatic Hydrocarbon Receptor Mediates Transactivation, Enhancer-Promoter Communication, and Changes in Chromatin Structure," *Molecular and Cellular Biology*, 16(1):430-436.
Ko et al., (Jul. 1997) "Transactivation Domains Facilitate Promoter Occupancy for the Dioxin-Inducible CYP1A1 Gene In Vivo," *Molecular and Cellular Biology*, 17(7):3497-3507.
Kron et al., (2009) "Discovery of novel hypermethylated genes in prostate cancer using genomic CpG island microarrays," *PLoS One*,4(3):e4830 (abstract only), 2 pages.
Kulis et al., (2010) "DNA methylation and cancer," *Advances in Genetics*, 70, 27-56 (Abstract only, 2 pages).
Kuo, M. Tien, (1979) "Studies in Heterochromatin DNA: Accessibility of Late Replicating Heterochromatin DNA in Chromatin to Micrococcal Nuclease Digestion," *Chromosoma (Berl.)* 70:183-194.
Kwabi-Addo et al., (2007) "Age-related DNA methylation changes in normal human prostate tissues," *Clin. Cancer Res.*, 13:3796-3802.
Laurent-Puig et al., (Nov. 2010) "Colorectal oncogenesis," *Bull Cancer*, 97(11):1311-21 (abstract only), 2 pages.
Lee et al., (2004) "PLP2/A4 interacts with CCR1 and stimulates migration of CCR1-expressing HOS cells," *Biochemical and Biophysical Research Communications*, 324:768-772.
Lewis, Matt "Agarose gel electrophoresis (basic method)," Loading Buffer Recipe from Matt Lewis—Methodbook.net [retrieved on Mar. 28, 2013 at http://www.methodbook.net/dna/agarogel.html#loadingbuff] copyright 2001, 5 pages.
Liu et al., (Jul. 2009) "Methylation status of RASSF1A and DAPK promoter in retinoblastoma," *Zhonghua YanKe Za Zhi.*, 45(7):631-5 (abstract only), 2 pages.

(56) References Cited

OTHER PUBLICATIONS

Liu et al., (May 27, 2009) "The 14-3-3sigma gene promoter is methylated in both human melanocytes and melanoma," *BMC Cancer*, 9:162 (abstract only), 2 pages.
Lyn-Cook et al., (Dec. 2010) "Gender differences in gemcitabine (Gemzar) efficacy in cancer cells: effect ofindole-3-carbinol," *Anticancer Res*.30(12):4907-13 (abstract only), 1 page.
Ma et al., (2010) "The relationship between methylation of the Syk gene in the promoter region and the genesis of lung cancer," *Clin Lab.*, 56(9-10):407-16 (abstract only), 2 pages.
Majid et al., (Jan. 1, 2010) "Genistein reverses hypermethylation and induces active histone modifications in tumor suppressor gene B-Cell translocation gene 3 in prostate cancer," *Cancer*, 116(1):66-76 (abstract only), 2 pages.
Martin et al., (Feb. 2010) "Epigenetic regulation of the non-canonical Wnt pathway in acute myeloid leukemia," *Cancer Sci.* 101(2):425-32 (abstract only), 2 pages.
Martinez et al., (May 16, 2009) "A microarray-based DNA methylation study of glioblastoma multiforme," *Epigenetics*, 4(4):255-64 (abstract only), 2 pages.
Masson et al. (Jul. 10, 1996) "Conditions favoring RNA polymerase 1 transcription in permeabilized cells," *Exp Cell Res*, 226(1):114-125.
Matarazzo et al., (Oct. 2004) "In vivo analysis of DNA methylation patterns recognized by specific proteins: coupling ChIP and bisulfate analysis," *Biotechniques*, 37(4):666-8, 670, 672-3.
Mathieu et al., (2002) "Methylation of a euchromatin-heterochromatin transition region in *Arabidopsis thaliana* chromosome 5 left arm," *Chromosome Research*, 10:455-466.
Meijer et al., (1996) "Use of Mitochondrial DNA as a Sensitive and Specific Marker for Localization of Mitochondria in Fractionated Plant Extracts," *Plant Molecular Biology Reporter*, 14(4):353-362.
Mellott et al., (2001) "Cytokine-induced changes in chromatin structure and in vivo footprints in the inducible NOS promoter," *Am. J Physiol. Lung Cell Mol. Physiol.*, 280:L390-L399.
Melotte et al., (Jul. 1, 2009) "N-Myc downstream-regulated gene 4 (NDRG4): a candidate tumor suppressor gene and potential biomarker for colorectal cancer," *J Natl Cancer Inst.*, 101(13):916-27 (abstract only), 2 pages.
Micard et al., (Jul. 1985) "Purification of RNA-free plasmid DNA using alkaline extraction followed by Ultrogel A2 column chromatography," *Anal Biochem.*, 148(1):121-126, Abstract, 2 pages.
Moncada-Pazos et al., (Aug. 15, 2009) "The ADAMTS12 metalloprotease gene is epigenetically silenced in tumor cells and transcriptionally activated in the stroma during progression of colon cancer," *J Cell Sci.* 122(Pt 16):2906-13 (abstract only), 2 pages.
Morris et al., (Mar. 24, 2011) "Genome-wide methylation analysis identifies epigenetically inactivated candidate tumour suppressor genes in renal cell carcinoma," *Oncogene*,30(12):1390-401 (abstract only), 2 pages.
Muggerud et al., (2010) "Frequent aberrant DNA methylation of ABCB1, FOXC1, PPP2R2B and PTEN in ductal carcinoma in situ and early invasive breast cancer," *Breast Cancer Res*, 12(1):R3, 10 pages.
Narita et al., (Jun. 13, 2003) "Rb-Mediated Geterochromatin Formation and Silencing of E2F Target Genes during Cellular Senescence," *Cell*, 113(6):703-716.
Niklinska et al., (2009) "Prognostic significance of DAPK and RASSF1A promoter hypermethylation in non-small cell lung cancer (NSCLC)," *Folia Histochem Cytobiol*. 47(2):275-80 (abstract only), 2 pages.
Nomoto et al., (Mar. 2010) "Epidermal growth factor-containing fibulin-like extracellular matrix protein 1, EFEMP1, a novel tumor-suppressor gene detected in hepatocellular carcinoma using double combination array analysis," *Ann Surg Oneal.*,17(3):923-32 (abstract only), 2 pages.
Nuovo et al., (Oct. 26, 1999) "*In situ* detection of the hypermethylation-induced inactivation of the p16 gene as an early event in oncogenesis," *Proc Natl Acad Sci USA*, 6(22): 12754-9.
Ogawa et al., (Jun. 6, 2008) "Intersection of the RNA Interference and X-Inactivation Pathways," *Science*, 320:1336-1341.
Okino et al., (2007) "Chromatin Changes on the *GSTP1* Promoter Associated with its Inactivation in Prostate Cancer," *Molecular Carcinogenesis*, 46(10):839-846.
Okino et al., (Jul. 1995) "Dioxin Induces Localized, Graded Changes in Chromatin Structure: Implications for Cyp1A1 Gene Transcription," *Molecular and Cellular Biology*, 15(7):3714-3721.
Okino et al., (Sep. 1998) "Hypoxia-inducible Mammalian Gene Expression Analyzed *in Vivo* at a TATA-driven Promoter and at an Initiator-driven Promoter," *Journal of Biological Chemistry*, 273(37):23837-23843.
Ozsolak et al., (Feb. 2007) "High-throughput mapping of the chromatin structure of human promoters," *Nature Biotechnology* 25(2): 244-249.
Paluszczak et al., (Feb. 2011) "Frequent gene hypermethylation in laryngeal cancer cell lines and the resistance to demethylation induction by plant polyphenols," *Toxicol In Vitro*. 25(1):213-21 (abstract only), 2 pages.
Park et al., (Jan. 2011) "Promoter CpG island hypermethylation during breast cancer progression," *Virchows Arch.*, 458(1):73-84 (abstract only), 2 pages.
Patel et al., (Oct. 1997) "Aberrant Silencing of the CpG Island-Containing Human $O^6$-Methylguanine DNA Methyltransferase Gene Is Associated with the Loss of Nucleosome-Like Positioning," *Molecular and Cellular Biology*, 17(10):5813-5822.
Pfeifer et al., (Jun. 1991) "Chromatin differences between active and inactive X chromosomes revealed by genomic footprinting of permeabilized ceils using DNase 1 and ligation-mediated PCR," *Genes Dev.*, 5(6):1102-1113.
Poetsch et al. (Feb. 2011) "Alterations in the tumor suppressor gene p16(INK4A) are associated with aggressive behavior of penile carcinomas," *Virchows Arch*. 458(2):221-9 (abstract only), 2 pages.
"Properties of Exonucleases and Endonucleases," *New England Biolabs, Inc*. [Retrieved at https://www.neb.com/tools-andresources/selection-charts/properties-of-exonucleases-and-endonucleases on Jul. 17, 2015], 2 pages.
Pulling et al., (Dec. 2009) "Dual promoter regulation of death-associated protein kinase gene leads to differentially silenced transcripts by methylation in cancer," *Carcinogenesis*, 30(12):2023-30 (abstract only), 2 pages.
Qian et al., (Jun. 2011) "Abnormal methylation of GRAF promoter Chinese patients with acute myeloid leukemia," *Leuk Res.*, 35(6):783-6 (abstract only), 2 pages.
QIAquick® Spin Handbook (sold by Qiagen®, published Mar. 2008, 44 pages).
Rao et al., (2001) "Chromatin Remodeling, Measured by a Novel Real-Time Polymerase Chain Reaction Assay, Across the Proximal Promoter Region of the *IL-2* Gene," *Journal of Immunology*, 167:4494-4503.
Rivero-Muller et al., (Feb. 13, 2007) "Mixed chelate copper complex, Casiopeina IIgly®, binds and degrades nucleic acids: A mechanism of cytotoxicity," *Chemico-Biological Interactions*, Elsevier Science, Ireland, 165(3):189-199.
Rodriguez-Campos et al., (Nov. 2007) "RNA is an integral component of chromatin that contributes to its structural organization," *Plos One* 2(11):e1182, 12 pages.
Röhrs et al., (Oct. 16, 2009) "Hypomethylation and expression of BEX2, IGSF4 and TIMP3 indicative of MLL translocations in acute myeloid leukemia," *Mol Cancer*, 8:86 (abstract only), 2 pages.
Ronai, D. et al., (Jan. 22, 2007) "Detection of chromatin-associated single-stranded DNA in regions targeted for somatic hypermutation," *J. Exp. Med.*, 204(1):181-190.
Sakamoto et al., (Apr. 2010) "MT1G hypermethylation: a potential prognostic marker for hepatoblastoma," *Pediatr Res.*,67(4):387-93 (abstract only), 2 pages.
Sambrook et al., (2001) "Protocol 1—Mapping Protein-binding Sites on DNA by DNase 1 Footprinting," and "Protocol 3—Mapping DNase-1-hypersensitive Sites," *Molecular Cloning: A Laboratory manual*, 3rd edition Cold Spring Harbor Laboratory Press, New York, Chapter 17, pp. 17.4-17.12 and 17.18-17.22, 14pp.
Sasahira et al., (Feb. 2011) "Downregulation of runt-related transcription factor 3 associated with poor prognosis of adenoid cystic

(56) References Cited

OTHER PUBLICATIONS and mucoepidermoid carcinomas of the salivary gland," *Cancer Sci.*, 102(2):492-7 (abstract only), 2 pages.

Schagdarsurengin et al., (Nov. 16, 2009) "Frequent epigenetic inactivation of RASSF10 in thyroid cancer," *Epigenetics*,4(8):571-6 (abstract only), 1 page.

Sharma et al., (2009) "Prognostic relevance of promoter hypermethylation of multiple genes in breast cancer patients," *Cell Oncol.*,31(6):487-500 (abstract only), 2 pages.

Shiokawa et al., (2007) Stage-specific expression of DNaseγ during B-cell development and its role in B-cell receptor-mediated apoptosis in WEHI-231 cells, *Cell Death and Differentiation*, 14(5):992-1000.

Steinmann et al., (Dec. 2009) "Frequent promoter hypermethylation of tumor-related genes in head and neck squamous cell carcinoma," *Oncol Rep.*22(6):1519-26 (abstract only), 2 pages.

Stephen et al., (Jan. 2009) "DNA hypermethylation profiles in squamous cell carcinoma of the vulva," *Int J Gynecol Pathol.*, 28(1):63-75 (abstract only), 2 pages.

Syeed et al., (Feb. 10, 2011) "Mutational and promoter hypermethylation status of FHIT gene in breast cancer patients of Kashmir," *Mutat Res.*, 707(1-2):1-8 (abstract only), 2 pages.

Tan et al. (2010) "Manipulation and Isolation of Single Cells and Nuclei," *Methods Cell Biol*, 98:79-96.

Tanguay et al., (1990) "PCR-aided DNaseI footprinting of single copy gene sequences in permeabilized cells," *Nucleic Acids Research*, 18(19):5902.

Tänzer et al., (Feb. 4, 2010) "Performance of epigenetic markers SEPT9 and ALX4 in plasma for detection of colorectal precancerous lesions," *PLoS One*, 5(2):e9061, 6 pages.

Thu et al., (2009) "Methylated DNA Immunoprecipitation," *Journal of Visualized Experiments*, 23 pp. 1-4; [http://www.jove.com/index/Details.stp?ID=935] DOI: 10.3791/935.

Tokuyama, (Dec. 2010) "Aberrant Methylation of Heparan Sulfate Glucosamine 3-O-Sulfotransferase 2 Genes as a Biomarker in Colorectal Cancer," *Anticancer Res*. 30(12):4811-4818.

Tomita et al., (Mar. 2011) "Inhibition of gastric carcinogenesis by the hormone gastrin is mediated by suppression of TFF1 epigenetic silencing," *Gastroenterology*, 140(3):879-91 (abstract only), 2 pages.

Tornaletti et al., (Dec. 1, 1996) "A High-Resolution Analysis of Chromatin Structure Along p53 Sequences," *Molecular Carcinogenesis*, 17(4):192-201.

Toyota et al., (1999) "CpG island methylator phenotypes in aging and cancer," *Seminars in Cancer Biology*, 9:349-357.

Tung et al., (Apr. 15, 2009) "HAI-2 is epigenetically downregulated in human hepatocellular carcinoma, and its Kunitz domain type 1 is critical for anti-invasive functions," *Int J Cancer.*, 124(8):1811-9 (abstract only), 2 pages.

Van Steensel et al., (2000) "Identification of in vivo DNA targets of chromatin proteins using tethered Dam methyltransferase," *Nature Biotechnology* 18:424-428.

Wang et al., (Oct. 19, 2009) "CHD5 is down-regulated through promoter hypermethylation in gastric cancer," *J Biomed Sci*. 16:95 (abstract only), 2 pages.

Wojdacz et al., (2007) "Methylation-sensitive high resolution melting (MS-HRM): a new approach for sensitive and high-throughput assessment of methylation," *Nucleic Acids Research*, 35(6):e41, 7 pages.

Wu et al., (Jun. 1, 2010) "Glutamate receptor, ionotropic, kainate 2 silencing by DNA hypermethylation possesses tumor suppressor function in gastric cancer," *Int J Cancer*,126(11):2542-52 (abstract only), 2 pages.

Xu, et al., (Feb. 2011) "BCL2L10 protein regulates apoptosis/proliferation through differential pathways in gastric cancer cells," *J Pathol*. 223(3):400-9 (abstract only), 2 pages.

Yao et al., (Jul. 2011) "Aberrant methylation of CCAAT/enhancer binding protein zeta promoter in acute myeloid leukemia," *Leuk Res.*, 35(7):957-60 (abstract only), 2 pages.

Yoon et al., (Apr. 12, 1996) "Poly(ADP-ribosyl)ation of Histone H1 Correlates with Internucleosomal DNA Fragmentation during Apoptosis," The *Journal of Biological Chemistry*, 271(15):9120-9134.

Yu et al., (May 28, 2009) "TSC-22 contributes to hematopoietic precursor cell proliferation and repopulation and is epigenetically silenced in large granular lymphocyte leukemia," *Blood*, 113(22):5558-67 (abstract only), 2 pages.

Zare et al., (Jan. 17, 2009) "Qualitative analysis of Adenomatous Polyposis Coli promoter: hypermethylation, engagement and effects on survival of patients with esophageal cancer in a high risk region of the world, a potential molecular marker," *BMC Cancer*, 9:24 (abstract only), 2 pages.

Zaret K.S., (1999) "*In Vivo* Analysis of Chromatin Structure," *Methods in Enzymology, Lnkd-Pubmed*, 304:612-626.

Zaret K., (2005) "Micrococcal Nuclease Analysis of Chromatin Structure," *Current Protocols in Molecular Biology*, Supplement 69:21.1.1-21.1.17.

Zhang et al., (1989) "In situ nucleoprotein structure at the SV40 major late promoter: melted and wrapped DNA flank the start site," *Genes and Development*, 3:1814-1822.

Zhang et al., (Nov. 2011) "The neuronal pentraxin II gene (NPTX2) inhibit proliferation and invasion of pancreatic cancer cells in vitro," *Mol Biol Rep.*, 38(8):4903-11 (abstract only), 2 pages.

Zimmermann et al., (2007) "The chromatin structure of the lysozyme GAS41 origin of DNA replication changes during the cell cycle," *Biol. Res.*, 40:185-192.

U.S. Office Action dated Jun. 2, 2017 issued in U.S. Appl. No. 15/427,845.

U.S. Notice of Allowance dated May 22, 2017 issued in U.S. Appl. No. 14/256,861.

U.S. Notice of Allowance dated Jul. 10, 2017 issued in U.S. Appl. No. 14/256,861.

U.S. Office Action dated Sep. 1, 2017 issued in U.S. Appl. No. 15/034,548.

Canadian Examination Report, dated Aug. 7, 2017, issued in Application No. CA 2,810,252.

Canadian Examination Report, dated May 15, 2017, issued in Application No. CA 2,810,520.

Chinese Office Action [Reexamination Decision] [no translation], dated Apr. 28, 2017, issued in Application No. CN 201280038451.3.

European Communication under Rule 71(3) EPC, Intention to grant, dated Mar. 15, 2017 issued in Application No. EP 11 824 170.2.

European Communication under Rule 71(3) EPC, Intention to grant, dated Sep. 1, 2017 issued in Application No. EP 11 824 170.2.

European Decision to grant a European patent pursuant to Article 97(1) EPC, dated Oct. 12, 2017 issued in Application No. EP 11 824 170.2.

European Decision to grant a European patent pursuant to Article 97(1) EPC, dated Jun. 22, 2017 issued in Application No. EP 12 819 299.4.

European Transmission of the certificate for a European patent pursuant to Rule 74 EPC, dated Jul. 20, 2017 issued in Application No. EP 12 819 299.4.

European Extended European Search Report dated Jun. 22, 2017 issued in Application No. EP 14 865 248.0.

Japanese Decision to Grant a Patent [no translation] dated Jan. 7, 2016 issued in Application No. JP 2013-528327.

Japanese Patent No. 5871933 B2 issued Jan. 22, 2016, (Patent Application No. JP 2013-528327), English translation of Allowed Claims, 3pp.

Japanese Decision to Grant a Patent [no translation] dated Apr. 4, 2016 issued in Application No. JP 2013-528325.

Japanese Patent No. 5917519 B2 issued Apr. 15, 2016, (Patent Application No. JP 2013-528325), English translation of Allowed Claims, 5pp.

Hamilton et al., (2006) "Use of Happy mapping for the higher order assembly of the *Tetrahytnena genome*," *Genomics*, 88:443-451.

Nguyen et al., (2001) "Altered chromatin structure associated with methylation-induced gene silencing in cancer cells: correlation of accessibility, methylation, MeCP2 binding and acetylation," *Nucleic Acids Research*, 29(22):4598-4606.

Pole et al. (2011) "Single-molecule analysis of genome rearrangements in cancer," *Nucleic Acids Research*, 39(13):e85, 13pp.

(56) References Cited

OTHER PUBLICATIONS

Shivaswamy et al., (2007) "Genome-wide analysis of chromatin status using tiling microarrays," *Methods*, 41:304-311.
Steensel et al., (Apr. 2000) "Identification of in vivo DNA targets of chromatin proteins using tethered Dam methyltransferase," *Nature Biotechnology*, 18:424-428.
Waalwijk et al., (Sep. 1978) MspI, an isoschizomer of HpaII which cleaves both unmethylated and methylated HpaII sites, *Nucleic Acids Research*, 5(9):3231-3236.
Wikipedia.com, "Algae," *Wikipedia, the free encyclopedia*, [retrieved on Mar. 4, 2016 at https://enwikipedia.org/wiki/Algae], 20pp.
Wikipedia.com, "Archaea," *Wikipedia, the free encyclopedia*, [retrieved on May 11, 2016 at https://enwikipedia.org/wiki/Archaea], 26pp.
Wikipedia.com, "Fish," *Wikipedia, the free encyclopedia*, [retrieved on Nov. 2, 2014 at https://enwikipedia.org/wiki/Fish], 11pp.
Wikipedia.com, "Fungus," "Fungi" redirects here, *Wikipedia, the free encyclopedia*, [retrieved on Jun. 3, 2013 at https://enwikipedia.org/wiki/Fungi], 28pp.
Wikipedia.com, "List of sequenced bacterial genomes," *Wikipedia, the free encyclopedia*, [retrieved on Jan. 24, 2014 at https://enwikipedia.org/wiki/List of sequenced bacterial genomes], 57pp.
Wikipedia.com, "Mammal," *Wikipedia, the free encyclopedia*, [retrieved on Sep. 22, 2011 at https://enwikipedia.org/wiki/Mammals], 17pp.
Wikipedia.com, "Murinae," *Wikipedia, the free encyclopedia*, [retrieved on Mar. 18, 2013 at https://enwikipedia.org/wiki/Murinae], 21pp.
Wikipedia.com, "Plant," *Wikipedia, the free encyclopedia*, [retrieved on Aug. 28, 2015 at https://enwikipedia.org/wiki/Plant], 14pp.
Wikipedia.com, "Protozoa," *Wikipedia, the free encyclopedia*, [retrieved on May 11, 2016 at https://enwikipedia.org/wiki/Protozoa], 10pp.
Wikipedia.com, "Viruses," *Wikipedia, the free encyclopedia*, [retrieved on Nov. 24, 2012 at https://enwikipedia.org/wiki/Virus], 34pp.
Wisegeek.com, "How Many Species of Bacteria Are There?" *wiseGEEK, clear answers for common questions*, [retrieved on Jan. 21, 2014 at https://wisegeek.org/how-many-species-of-bacteria-are-there.htm], 2pp.
U.S. Final Office Action dated Nov. 14, 2017 issued in U.S. Appl. No. 15/427,845.
Porteus et al. (Aug. 2005) "Gene targeting using zinc finger nucleases," *Nature Biotechnology*, 23(8):967-973.
U.S. Office Action dated Mar. 1, 2018 issued in U.S. Appl. No. 15/043,552.
U.S. Final Office Action dated Sep. 7, 2018 issued in U.S. Appl. No. 15/043,552.
U.S. Office Action dated Aug. 7, 2018 issued in U.S. Appl. No. 15/427,845.
Canadian Examination Report, dated Apr. 10, 2018, issued in Application No. CA 2,810,252.
Canadian Examination Report, dated Mar. 29, 2018, issued in Application No. CA 2,810,520.
European First Office Action dated May 7, 2018 issued in Application No. EP 14865248.0.
Munder, et al., (1979) "Lysophosphatidylcholine (Lysolecithin) and its Synthetic Analogues. Immunomodulating and Other Biologic Effects*" Springer Semin. Immunopathol., vol. 2, pp. 187-203.
Ravel et al., (2000) "Cloning and Sequence Analysis of the Mercury Resistance Operon of Streptomyces sp. Strain CHR28 Reveals a Novel Putative Second Regulatory Gene" Journal of Bacteriology, vol. 182, No. 8, Apr. 2000, pp. 2345-2349.
Smith, et al., (1979) "Intracellular pH and Its Regulation," Annual Review, Plant. Physiol., vol. 30, pp. 289-311.
Surzycki, S., (ed)(2003) "Appendix, in Human Molecular Biology Laboratory," Blackwell Science Ltd., pp. 215-222. <doi: 10.1002/9780470999257.appl>.
U.S. Office Action dated Jan. 11, 2019 issued in U.S. Appl. No. 15/043,552.
Digitonin [Webpage] Sigma-Aldrich: Digitonin, pp. 1-4. [retrieved on Jan. 6, 2019] <URL:https://.sigmaaldrich.com/catalog/ product/sigma/d 141?lang=en&region=US>.
Itaya et al. (1991) "Selective cloning of genes encoding Rnase H from *Salmonella typhimurium*, *Saccharomyces cerevisiae* and *Escherichia coli rnh* mutant" Molecular and General Genetics MGG, vol. 227, No. 3, pp. 438-445. <URL:https://doi.org/10.1007/BF00273935>.
Orczyk et al. (Mar. 2017) "Disordering Effects of Digitonin on Phospholipid Monolayers" Langmuir, vol. 33, No. 15, pp. 3871-3881. <doi: 10.1021/acs.langmuir.6b04613>.
U.S. Final Office Action dated Aug. 16, 2019 issued in U.S. Appl. No. 15/043,552.
U.S. Office Advisory Action dated Oct. 24, 2019 issued in U.S. Appl. No. 15/043,552.
Ohno et al., (Jan. 2002) "Triplex-forming DNAs in the human interphase nucleus visualized in situ by polypurine/polypyrimidine DNA probes and antitriplex antibodies" Chromosoma, vol. 111, pp. 201-213.

\* cited by examiner

DETECTING METHYLATION IN A SUBPOPULATION OF GENOMIC DNA

CROSS REFERENCE TO RELATED APPLICATIONS

This application is a continuation of U.S. application Ser. No. 13/396,496, filed on Feb. 14, 2012, abandoned, which claims the benefit from U.S. Provisional Application No. 61/442,918, filed on Feb. 15, 2011, both of which are hereby incorporated herein in their entireties for all purposes.

FIELD OF THE INVENTION

The present invention relates to methods for determining the methylation status of a subpopulation of genomic DNA in a biological sample.

BACKGROUND OF THE INVENTION

Most DNA in a cell is packaged around a set of histone proteins in a coiled structure known as a nucleosome. Nucleosomes, in turn, are further coiled into a highly condensed structure that tightly compacts the DNA. This combination of DNA and protein packaging is generally referred to as chromatin. Chromatin has two forms: euchromatin, a loosely packaged form of chromatin in which the DNA is accessible to transcriptional machinery and is usually, but not always, transcriptionally active, and heterochromatin, a tightly packaged form in which the DNA is inaccessible to transcriptional machinery and is usually, but not always, transcriptionally silent.

The transition between euchromatin and heterochromatin is mainly controlled by three epigenetic events, DNA methylation, histone modification, and RNA interaction. These epigenetic events affect whether genomic DNA in a cell is in a loosely packaged, transcriptionally active form or a tightly packaged, transcriptionally silent form.

SUMMARY OF THE INVENTION

The present invention provides methods of detecting a biological, pathological, genetic or epigenetic state of a subpopulation of genomic DNA (gDNA) in a sample. In some embodiments, the methods comprise:

a) dividing a biological sample comprising gDNA into at least a first portion and a second portion;

b) enriching a subpopulation of gDNA in the first portion; and c) determining the DNA methylation status at one or more gDNA regions in the first portion and in the second portion, wherein a difference in the extent of DNA methylation in the subpopulation of gDNA in the first portion relative to the extent of DNA methylation in the second portion at the one or more gDNA regions indicates or is correlated with the biological, pathological, genetic or epigenetic state in the subpopulation of gDNA.

In a related aspect, the invention provides methods of detecting the presence of cancer in a biological sample. In some embodiments, the methods comprise:

a) dividing a biological sample comprising gDNA, wherein the biological sample comprises cells suspected of being cancerous, into at least a first portion and a second portion;

b) enriching a subpopulation of gDNA in the first portion; and c) determining the DNA methylation status at one or more gDNA regions in the first portion and in the second portion, wherein a difference in the extent of DNA methylation in the enriched gDNA in the first portion relative to the extent of DNA methylation in the gDNA in the second portion at the one or more gDNA regions indicates or is correlated with the presence of cancer in the biological sample.

In a related aspect, the invention provides methods of detecting the presence of cancer in a biological sample. In some embodiments, the methods comprise:

a) dividing a biological sample comprising gDNA, wherein the biological sample comprises cells suspected of being cancerous, into at least a first portion and a second portion;

b) enriching for inaccessible gDNA in the first portion; and c) determining the DNA methylation status at one or more gDNA regions in the first portion and in the second portion, wherein a difference in the extent of DNA methylation in the inaccessible gDNA in the first portion relative to the extent of DNA methylation in the gDNA in the second portion at the one or more gDNA regions indicates or is correlated with the presence of cancer in the biological sample. In some embodiments, an increase in the extent of DNA methylation in the inaccessible gDNA in the first portion relative to the extent of DNA methylation in the gDNA in the second portion at the one or more gDNA regions indicates or is correlated with the presence of cancer in the biological sample.

In a related aspect, the invention provides methods of detecting the presence of cancer in a biological sample. In some embodiments, the methods comprise:

a) dividing a biological sample comprising gDNA, wherein the biological sample comprises cells suspected of being cancerous, into at least a first portion and a second portion;

b) enriching for accessible gDNA in the first portion; and c) determining the DNA methylation status at one or more gDNA regions in the first portion and in the second portion, wherein a difference in the extent of DNA methylation in the accessible gDNA in the first portion relative to the extent of DNA methylation in the gDNA in the second portion at the one or more gDNA regions indicates or is correlated with the presence of cancer in the biological sample. In some embodiments, an increase in the extent of DNA methylation in the accessible gDNA in the first portion relative to the extent of DNA methylation in the gDNA in the second portion at the one or more gDNA regions indicates or is correlated with the presence of cancer in the biological sample.

In a related aspect, the invention provides methods of detecting the presence of cancer in a biological sample. In some embodiments, the methods comprise:

a) dividing a biological sample comprising gDNA, wherein the biological sample comprises cells suspected of being cancerous, into at least a first portion and a second portion;

b) enriching the first portion by performing chromatin immunoprecipitation ("ChIP"); and c) determining the DNA methylation status at one or more gDNA regions in the first portion and in the second portion, wherein a difference in the extent of DNA methylation in the ChIP-enriched first portion relative to the extent of DNA methylation in the gDNA in the second portion at the one or more gDNA regions indicates or is correlated with the presence of cancer in the biological sample. In some embodiments, an increase in the extent of DNA methylation in the ChIP-enriched first portion relative to the extent of DNA methylation in the gDNA in the second portion at the one or more gDNA regions indicates or is correlated with the presence of cancer in the biological sample. In various embodiments, ChIP enrichment can be for gDNA associated with or bound to histones containing a modification of interest (e.g., trimethylation of lysine 4 of histone 3) or gDNA associated with or bound to a protein of interest (e.g., RNA polymerase II).

In a further aspect, the invention provides methods of determining genomic imprinting of a preselected gDNA region in a biological sample. In some embodiments, the methods comprise:

a) dividing a biological sample comprising gDNA into at least a first portion and a second portion;

b) enriching for inaccessible gDNA in the first portion and retaining total gDNA in the second portion; and c) determining the DNA methylation status at the preselected gDNA region in the first portion and in the second portion, wherein an extent of DNA methylation in the inaccessible gDNA in the first portion that is about 100% and the extent of DNA methylation in the total gDNA in the second portion is about 50% at the preselected gDNA region indicates or is correlated with proper imprinting of the preselected gDNA region, and wherein an extent of DNA methylation in the inaccessible gDNA in the first portion that is less than about 100% (e.g., less than about 90%, 85%, 80%, 75%) and the extent of DNA methylation in the total gDNA in the second portion is about 50% at the preselected gDNA region indicates or is correlated with loss of imprinting of the preselected gDNA region.

In a further aspect, the invention provides methods of determining genomic imprinting of a preselected gDNA region in a biological sample. In some embodiments, the methods comprise:

a) dividing a biological sample comprising gDNA into at least a first portion and a second portion;

b) enriching for accessible gDNA in the first portion and retaining total gDNA in the second portion; and c) determining the DNA methylation status at the preselected gDNA region in the first portion and in the second portion, wherein an extent of DNA methylation in the accessible gDNA in the first portion that is about 100% and the extent of DNA methylation in the total gDNA in the second portion is about 50% at the preselected gDNA region indicates or is correlated with proper imprinting of the preselected gDNA region, and wherein an extent of DNA methylation in the accessible gDNA in the first portion that is less than about 100% (e.g., less than about 90%, 85%, 80%, 75%) and the extent of DNA methylation in the total gDNA in the second portion is about 50% at the preselected gDNA region indicates or is correlated with loss of imprinting of the preselected gDNA region.

In a further aspect, the invention provides methods of determining genomic imprinting of a preselected gDNA region in a biological sample. In some embodiments, the methods comprise:

a) dividing a biological sample comprising gDNA into at least a first portion and a second portion;

b) enriching the first portion by performing ChIP and retaining total gDNA in the second portion; and c) determining the DNA methylation status at the preselected gDNA region in the first portion and in the second portion, wherein an extent of DNA methylation in the ChIP-enriched gDNA in the first portion that is about 100% and the extent of DNA methylation in the total gDNA in the second portion is about 50% at the preselected gDNA region indicates or is correlated with proper imprinting of the preselected gDNA region, and wherein an extent of DNA methylation in the ChIP-enriched gDNA in the first portion that is less than about 100% (e.g., less than about 90%, 85%, 80%, 75%) and the extent of DNA methylation in the total gDNA in the second portion is about 50% at the preselected gDNA region indicates or is correlated with loss of imprinting of the preselected gDNA region. In various embodiments, ChIP enrichment can be for gDNA associated with or bound to histones containing a modification of interest (e.g., trimethylation of lysine 4 of histone 3) or gDNA associated with or bound to a protein of interest (e.g., RNA polymerase II).

In a related aspect, the invention provides methods of determining genomic imprinting of a preselected gDNA region in a biological sample, the method comprising:

a) dividing a biological sample comprising gDNA into at least a first portion and a second portion;

b) enriching for accessible gDNA in the first portion and retaining total gDNA in the second portion; and c) determining the DNA methylation status at the preselected gDNA region in the first portion and in the second portion, wherein an extent of DNA methylation in the accessible gDNA in the first portion that is about 0% (e.g., less than about 5%) and the extent of DNA methylation in the total gDNA in the second portion that is about 50% at the preselected gDNA region indicates or is correlated with proper imprinting of the preselected gDNA region.

In another aspect, the invention provides methods of detecting a biological, pathological, genetic or epigenetic state of accessible gDNA in a sample. In some embodiments, the methods comprise:

a) dividing a biological sample comprising gDNA into at least a first portion and a second portion;

b) enriching for accessible gDNA in the first portion and retaining total gDNA in the second portion; and c) determining the DNA methylation status at one or more gDNA regions in the first portion and in the second portion, wherein a difference in the extent of DNA methylation in the subpopulation of gDNA in the first portion relative to the extent of DNA methylation in the total gDNA in the second portion at the one or more gDNA regions indicates or is correlated with the biological, pathological, genetic or epigenetic state in the subpopulation of gDNA.

In another aspect, the invention provides methods of detecting a biological, pathological, genetic or epigenetic state of inaccessible gDNA in a sample. In some embodiments, the methods comprise:

a) dividing a biological sample comprising gDNA into at least a first portion and a second portion;

b) enriching for inaccessible gDNA in the first portion and retaining total gDNA in the second portion; and c) determining the DNA methylation status at one or more gDNA regions in the first portion and in the second portion, wherein a difference in the extent of DNA methylation in the subpopulation of gDNA in the first portion relative to the extent of DNA methylation in the total gDNA in the second portion at the one or more gDNA regions indicates or is correlated with the biological, pathological, genetic or epigenetic state in the subpopulation of gDNA.

In another aspect, the invention provides methods of detecting a biological, pathological, genetic or epigenetic state of ChIP-enriched gDNA in a sample. In some embodiments, the methods comprise:

a) dividing a biological sample comprising gDNA into at least a first portion and a second portion;

b) enriching for ChIP-enriched gDNA in the first portion and retaining total gDNA in the second portion; and c) determining the DNA methylation status at one or more gDNA regions in the first portion and in the second portion, wherein a difference in the extent of DNA methylation in the subpopulation of gDNA in the first portion relative to the extent of DNA methylation in the total gDNA in the second portion at the one or more gDNA regions indicates or is correlated with the biological, pathological, genetic or epigenetic state in the subpopulation of gDNA. In various embodiments, ChIP enrichment can be for gDNA associated with or bound to histones containing a modification of interest (e.g., trimethylation of lysine 4 of histone 3) or gDNA associated with or bound to a protein of interest (e.g., RNA polymerase II).

With respect to the embodiments, in some embodiments, the methods further comprising the step of obtaining the biological sample. In some embodiments, the biological sample comprises isolated nuclei. In some embodiments, the biological sample is a population of cells. As needed or appropriate, the population of cells is treated with a permeabilization agent prior to the enrichment step b). The population of cells may also be treated with a DNA modification agent, e.g., an enzyme, a chemical or a drug that modifies DNA, prior to enrichment step b). In some embodiments, the population of cells is treated with a permeabilization agent and a DNA modification agent prior to the enrichment step b). In various embodiments, the population of cells can be in situ. In some embodiments, the biological sample is a solid tissue sample.

In some embodiments, an in situ treatment step is performed prior to the enriching step. For example, the gDNA may be subject to DNA cleavage, DNA modification or cross-linking (e.g., for carrying out chromatin immunoprecipitation ("ChIP")).

In some embodiments, the enriching step comprises enriching for accessible chromatin. Accessible gDNA can be enriched by any method in the art. Generally, the gDNA in the biological sample is modified with the modifying agent and the modified gDNA is purified, thereby yielding the first portion. For example, in various embodiments, the accessible gDNA can be enriched by contacting the DNA with a DNA modifying agent and then isolating modified DNA, e.g., via affinity purification based on the modification. The modification is preferably a non-native or non-naturally occurring modification. An illustrative modification is DNA methylation. The DNA methylation enzyme can modify cytosine at the 4 or 6 position or adenine at the 6 position. Other DNA modification enzymes may be utilized and may methylate other bases at different positions. In some embodiments, the modifying agent is a methylation agent that methylates adenine. In some embodiments, the accessible gDNA can be enriched by contacting the gDNA with an adenine methyltransferase, and then isolating gDNA modified with 6-methyladenine (6-mA).

In some embodiments, the enriching step comprises enriching for inaccessible chromatin. Inaccessible gDNA can be enriched by any method in the art. For example, in various embodiments, inaccessible gDNA is enriched by concurrently contacting the biological sample with a modifying agent and a cell membrane disrupting agent, and purifying the modified gDNA, thereby yielding the first portion. In some embodiments, the modifying agent is an enzyme, chemical or drug that cleaves DNA. Examples of enzymes include nucleases such as DNase I and restriction enzymes. In some embodiments, the modifying agent is a DNA nuclease, e.g., DNase I or Mnase. In some embodiments, the modifying agent is a restriction enzyme. In some embodiments, the modifying agent is an enzyme, chemical or drug that modifies DNA.

In some embodiments, the methods further comprise the step of performing chromatin immunoprecipitation ("ChIP"). For example, enrichment can be for gDNA associated with or bound to histones containing a modification of interest (e.g., trimethylation of lysine 4 of histone 3) or gDNA associated with or bound to a protein of interest (e.g., RNA polymerase II).

The second portion oftentimes represents a control. The control may be gDNA from a biological sample that has been treated (e.g., with a pharmacological agent or drug) or gDNA from an untreated biological sample. In some embodiments, the second portion comprises total gDNA.

The extent of methylation can be determined using any method known in the art. For example, in various embodiments, the extent of DNA methylation status is determined via restriction enzyme analysis, e.g., using methylation-sensing restriction enzymes. As understood by those of skill and described herein, restriction enzymes that sense DNA methylation, e.g., methylation-sensitive and/or methylation-dependent enzymes find use. In other embodiments, the extent of DNA methylation status is determined by contacting the gDNA with bisulfite and detecting methylation of bisulfite-modified gDNA, e.g., using any appropriate technique. As understood by those of skill and described herein, bisulfite modification is performed and the extent of DNA methylation can then be determined by various techniques, including without limitation Methylation Specific PCR ("MSP"), COBRA (as described by Xiong and Laird, *Nucleic Acids Res.* (1997) 25(12):2532-4), DNA sequencing, etc. In some embodiments, the extent of DNA methylation status is determined via affinity purification, e.g., using protein binding or direct or indirect antibody detection. For example, as understood by those of skill and described herein, antibodies that directly bind to methylated DNA bases find use to immunoprecipitate methylated DNA. The immunoprecipitated genomic regions (and containing methylated DNA) can be detected using known techniques, e.g., PCR, DNA sequencing, microarray, etc. Also, proteins that bind with high affinity to methylated gDNA, e.g., MBD proteins or MeCP2, can be used for affinity purification of methylated DNA. Antibodies that bind to such proteins bound to methylated gDNA also can be used to immunoprecipitate methylated DNA. In other embodiments, the extent of DNA methylation status is determined via direct nucleic acid sequencing. For example, single-molecule, real-time (SMRT) DNA sequencing or nanopore sequencing finds use to directly detect DNA methylation.

In some embodiments, the extent of methylation at the one or more gDNA regions in the first portion is higher than the extent of methylation at the one or more gDNA regions in the second portion. In some embodiments, the extent of methylation at the one or more gDNA regions in the first portion is lower than the extent of methylation at the one or more gDNA regions in the second portion.

Definitions

The term "biological sample" refers to any sample comprising genomic DNA.

"Permeabilizing," a cell membrane, as used herein, refers to reducing the integrity of a cell membrane to allow for entry of a modifying agent into the cell. A cell with a permeabilized cell membrane will generally retain the cell membrane such that the cell's structure remains substantially intact. In contrast, "disrupting" a cell membrane, as used herein, refers to reducing the integrity of a cell membrane such that the cell's structure does not remain intact. For example, contacting a cell membrane with a nonionic detergent will remove and/or dissolve a cell membrane, thereby allowing access of a modifying agent to genomic DNA that retains at least some chromosomal structure.

A "DNA modifying agent," as used herein, refers to a molecule that alters DNA in a detectable manner. For example, addition or removal of chemical moieties from the DNA are modifications. DNA modifying agents that do not result in DNA cleavage include, but are not limited to, DNA methylases or methyltransferases.

A "DNA cleaving agent," as used herein, refers to a molecule that cleaves DNA. For example, a DNA cleaving agent can cause DNA nicking or cleavage.

A "DNA region," as used herein, refers to a target sequence of interest within genomic DNA. The DNA region can be of any length that is of interest. In some embodiments, the DNA region is accessible by the DNA modifying agent being used. In some embodiments, the DNA region can include a single base pair, but can also be a short segment of sequence within genomic DNA (e.g., 2-100, 2-500, 50-500 bp) or a larger segment (e.g., 100-10,000, 100-1000, or 1000-5000 bp). In some embodiments, the amount of DNA in a DNA region is determined by the amount of sequence to be amplified in a PCR reaction. For example, standard PCR reactions generally can amplify between about 35 to 5000 base pairs. Alternatively, a DNA region can be a gene or chromosomal region of interest.

A different "extent" of modifications refers to a different number (actual or relative) of modified copies of one or more DNA regions between samples or between two or more DNA regions in one or more samples. For example, if 100 copies of two DNA regions (designated for convenience as "region A" and "region B") are each present in chromosomal DNA in a cell, an example of modification to a different extent would be if 10 copies of region A were modified whereas 70 copies of region B were modified.

The terms "oligonucleotide" or "polynucleotide" or "nucleic acid" interchangeably refer to a polymer of monomers that can be corresponded to a ribose nucleic acid (RNA) or deoxyribose nucleic acid (DNA) polymer, or analog thereof. This includes polymers of nucleotides such as RNA and DNA, as well as modified forms thereof, peptide nucleic acids (PNAs), locked nucleic acids (LNATM), and the like. In certain applications, the nucleic acid can be a polymer that includes multiple monomer types, e.g., both RNA and DNA subunits.

A nucleic acid is typically single-stranded or double-stranded and will generally contain phosphodiester bonds, although in some cases, as outlined herein, nucleic acid analogs are included that may have alternate backbones, including, for example and without limitation, phosphoramide (Beaucage et al. (1993) Tetrahedron 49(10):1925 and the references therein; Letsinger (1970) J. Org. Chem. 35:3800; Sprinzl et al. (1977) Eur. J. Biochem. 81:579; Letsinger et al. (1986) Nucl. Acids Res. 14: 3487; Sawai et al. (1984) Chem. Lett. 805; Letsinger et al. (1988) J. Am. Chem. Soc. 110:4470; and Pauwels et al. (1986) Chemica Scripta 26:1419), phosphorothioate (Mag et al. (1991) Nucleic Acids Res. 19:1437 and U.S. Pat. No. 5,644,048), phosphorodithioate (Briu et al. (1989) J. Am. Chem. Soc. 111:2321), O-methylphophoroamidite linkages (Eckstein, Oligonucleotides and Analogues: A Practical Approach, Oxford University Press (1992)), and peptide nucleic acid backbones and linkages (Egholm (1992) J. Am. Chem. Soc. 114:1895; Meier et al. (1992) Chem. Int. Ed. Engl. 31:1008; Nielsen (1993) Nature 365:566; and Carlsson et al. (1996) Nature 380:207), which references are each hereby incorporated herein by reference. Other analog nucleic acids include those with positively charged backbones (Denpcy et al. (1995) Proc. Natl. Acad. Sci. USA 92:6097); non-ionic backbones (U.S. Pat. Nos. 5,386,023, 5,637,684, 5,602,240, 5,216,141 and 4,469,863; Angew (1991) Chem. Intl. Ed. English 30: 423; Letsinger et al. (1988) J. Am. Chem. Soc. 110:4470; Letsinger et al. (1994) Nucleoside & Nucleotide 13:1597; Chapters 2 and 3, ASC Symposium Series 580, "Carbohydrate Modifications in Antisense Research", Ed. Y. S. Sanghvi and P. Dan Cook; Mesmaeker et al. (1994) Bioorganic & Medicinal Chem. Lett. 4: 395; Jeffs et al. (1994) J. Biomolecular NMR 34:17; Tetrahedron Lett. 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghvi and P. Dan Cook, which references are each hereby incorporated herein by reference. Nucleic acids containing one or more carbocyclic sugars are also included within the definition of nucleic acids (Jenkins et al. (1995) Chem. Soc. Rev. pp 169-176, which is incorporated by reference). Several nucleic acid analogs are also described in, e.g., Rawls, C & E News Jun. 2, 1997 page 35, which is incorporated by reference. These modifications of the ribose-phosphate backbone may be done to facilitate the addition of additional moieties such as labeling moieties, or to alter the stability and half-life of such molecules in physiological environments.

In addition to naturally occurring heterocyclic bases that are typically found in nucleic acids (e.g., adenine, guanine, thymine, cytosine, and uracil), nucleic acid analogs also include those having non-naturally occurring heterocyclic or other modified bases, many of which are described, or otherwise referred to, herein. In particular, many non-naturally occurring bases are described further in, e.g., Seela et al. (1991) Helv. Chim. Acta 74:1790, Grein et al. (1994) Bioorg. Med. Chem. Lett. 4:971-976, and Seela et al. (1999) Helv. Chim. Acta 82:1640, which are each incorporated by reference. To further illustrate, certain bases used in nucleotides that act as melting temperature (Tm) modifiers are optionally included. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, entitled "SYNTHESIS OF 7-DEAZA-2'-DEOXYGUANOSINE NUCLEOTIDES," which issued Nov. 23, 1999 to Seela, which is incorporated by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methyl cytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like.

"Accessibility" of a DNA region or "accessible DNA" interchangeably refers to the ability of a particular DNA region in a chromosome of a cell to be contacted and modified by a particular DNA cleaving or modifying agent. Without intending to limit the scope of the invention, it is believed that the particular chromatin structure comprising the DNA region will affect the ability of a DNA cleaving or modifying agent to cleave or modify the particular DNA region. For example, the DNA region may be wrapped around histone proteins and further may have additional nucleosomal structure that prevents, or reduces access of, the DNA cleaving or modifying agent to the DNA region of interest. Accessibility can therefore be detected as a function of the quantity of cleavage or modification. Relative accessibility between two DNA regions can be determined by comparing (e.g., generating a ratio) of cleavage or modification levels between the two regions.

A "heterologous sequence" or a "heterologous nucleic acid", as used herein, is one that originates from a source foreign to the particular host cell, or, if from the same source, is modified from its original form. Thus, a heterologous expression cassette in a cell is an expression cassette that is not endogenous to the particular host cell, for example by being linked to nucleotide sequences from an expression vector rather than chromosomal DNA, being linked to a heterologous promoter, being linked to a reporter gene, etc.

A "Type II-S restriction enzyme" is used with its usual meaning the art and refers to a restriction enzyme that recognizes a particular recognition sequence in DNA and then cleaves the DNA molecule outside of that recognition sequence. Exemplary Type II-S restriction enzymes include, but are not limited to, MnII, FokI, and AlwI.

The term "individual," "patient,", "subject" interchangeably refer to a mammal, for example, a human, a non-human primate, a domesticated mammal (e.g., a canine or a feline), an agricultural mammal (e.g., equine, bovine, ovine, porcine), or a laboratory mammal (e.g., rattus, murine, lagomorpha, hamster).

The terms "direct" or "directly" interchangeably refer to the performance of two contiguous method steps without performing any intervening method steps.

DETAILED DESCRIPTION

1. Introduction

Figure 1:
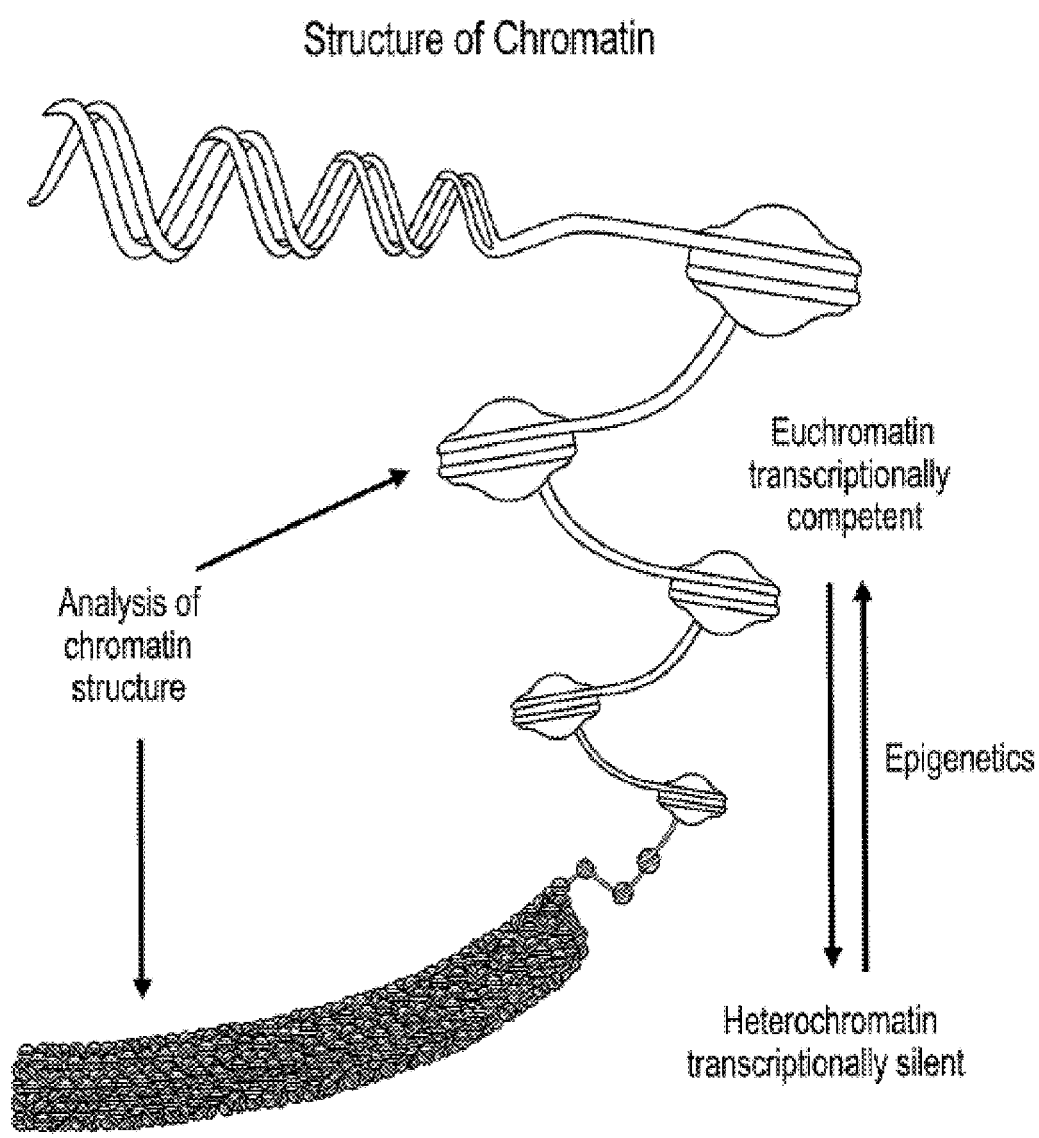
FIG. 1 illustrates a schematic representation of the chromatin. Eukaryotic DNA can be classified into two general states, euchromatin, where the DNA is loosely packaged, accessible and transcriptionally competent and heterochromatin, where the DNA is tightly packaged, inaccessible and transcriptionally silent. Epigenetics controls the transition between these two states.
Figure 2:
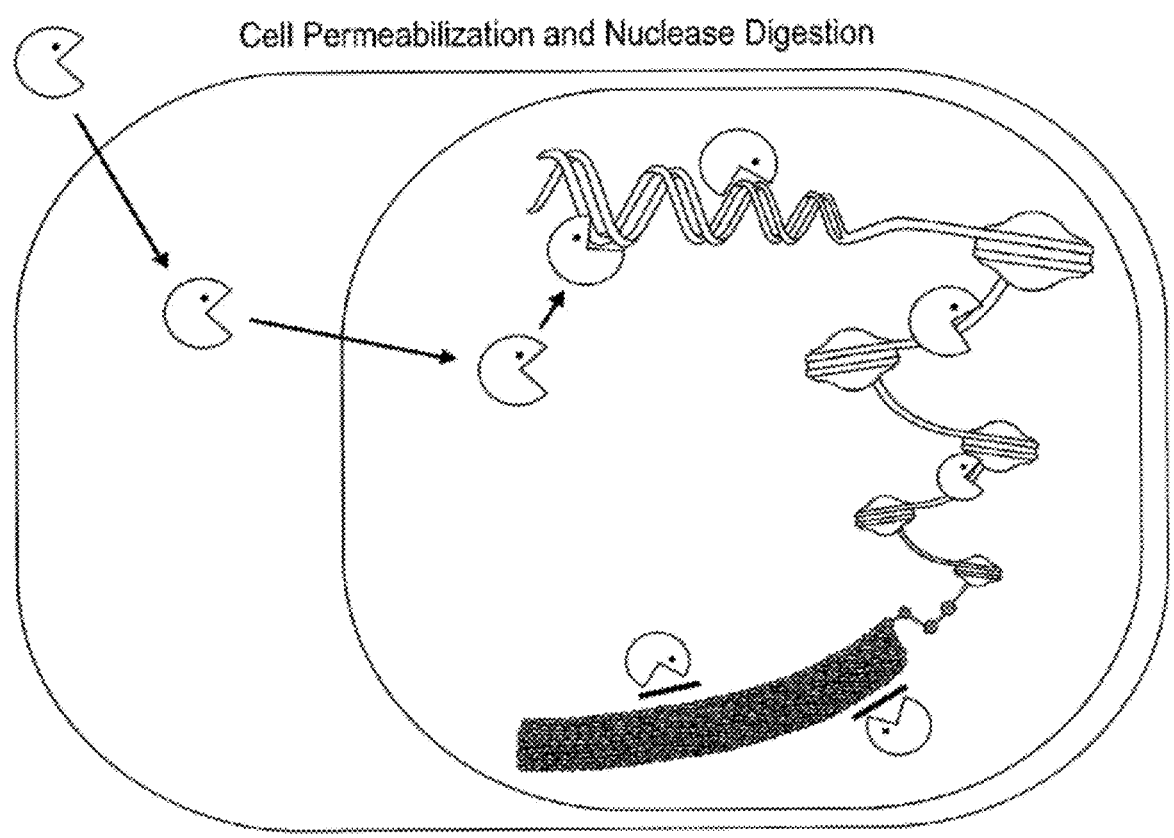
FIG. 2 illustrates a schematic representation of a procedure for the isolation of the subpopulation of gDNA that corresponds to inaccessible chromatin. Cells are treated with a buffer that permeabilizes the cell and contains a nuclease. The nuclease diffuses into the cell, enters the nucleus and digests accessible chromatin, but inaccessible chromatin (represented as a thick line towards the bottom of the Figure) is not digested. After gDNA purification, DNA that was originally in an inaccessible chromatin configuration will be enriched relative to DNA that was originally in an accessible chromatin configuration.

The present invention provides processes by which a difference in the DNA methylation state of a genomic DNA region can be identified in a subpopulation of genomic DNA (gDNA). The DNA methylation status in the subpopulation can be determined relative to the total gDNA population or relative to the same enriched subpopulation in a parallel sample, e.g., of a control sample, e.g., that is of a different physiological/pathophysiological state or that has been treated or untreated with an agent (e.g., a pharmacological agent or drug). The relative DNA methylation information of the gDNA subpopulation can provide insight on, e.g., epigenetic changes in a subpopulation of cells and/or epigenetic differences between two alleles.

The identification of epigenetic changes in a subpopulation of cells can have significant biomedical relevance. For example, analysis of biopsy samples may identify a subpopulation of gDNA that has an aberrant DNA methylation profile. Such information may indicate or is correlated with the presence of a malignancy or pre-neoplastic lesion in a background of healthy cells.

The identification of epigenetic differences between the two alleles can also have biomedical relevance. Such information can determine if a specific genomic region is properly imprinted (one allele is active and the other is epigenetically silenced); imprinting defects are associated with numerous genetic disorders. This information can also detect loss of imprinting, a phenomena associated with the development and progression of several cancers.

The present invention identifies differences in DNA methylation employing two general steps: (1) enrichment of a subpopulation of gDNA and (2) analysis and comparison of relative DNA methylation in the subpopulation of gDNA relative to a reference population of gDNA, e.g., to the DNA methylation of total gDNA or a control sample of the same subpopulation of gDNA. Enrichment of a subpopulation of gDNA prior to analyzing the extent, quality or patterning of methylation provides superior detection sensitivity in comparison to established methodologies. For example, the present methods can detect cancer in a biopsy sample which contains a small portion (e.g., 1% or less) of cancerous cells. A tumor biopsy can be effectively screened for a DNA methylation biomarker that is found in cancerous cells but not in normal tissue, e.g., the GSTP1 promoter.

The present methods offer advantages over the established methodologies. This is because the accessible or inaccessible subpopulation of genomic DNA may be enriched for DNA associated with cancerous cells. Performing the present methods, it is possible to observe over 99% nuclease digestion of accessible DNA regions. Thus, in a biopsy sample that is 1% cancerous, a DNA methylation biomarker that is associated with inaccessible DNA will be enriched 50-fold after nuclease digestion of accessible DNA.

2. Obtaining, Processing and Dividing a Biological Sample

The methods evaluate genomic DNA in a biological sample. In various embodiments, the biological sample can comprise body fluids, tissues, cells, isolated nuclei or isolated genomic DNA. In some embodiments, the methods further comprise the step of obtaining the biological sample or samples.

In some embodiments, the biological sample comprises cells. A variety of eukaryotic cells can be used in the present invention. In some embodiments, the cells are animal cells, including but not limited to, human, or non-human, mammalian cells. Non-human mammalian cells include but are not limited to, primate cells, mouse cells, rat cells, porcine cells, and bovine cells. In some embodiments, the cells are plant cells. Cells can be, for example, cultured primary cells, immortalized culture cells or can be from a biopsy or tissue sample, optionally cultured and stimulated to divide before assayed. Cultured cells can be in suspension or adherent. Cells can be from animal tissues, biopsies, etc. For example, the cells can be from a tumor biopsy, a hair bulb, a cheek swab or another solid tissue sample. In some embodiments, the biological sample is a fluid sample. For example, the biological sample can be from blood, serum, plasma, semen, urine, saliva, amniotic fluid, or a tissue/cell culture suspension.

In some embodiments, the biological sample is from a tissue suspected of being cancerous. In various embodiments, the biological sample is from a biopsy, for example, solid tissue, for example, an epithelial tissue. Exemplary epithelial tissues include without limitation thyroid, adrenal gland, bladder, uterus, breast, prostate, testicular, liver, lung, cervical, ovary, skin, gastrointestinal, colorectal, kidney, bladder, pancreas, stomach, brain, esophagus tissue, etc. In the case of suspected hematological cancers, the biological sample can be a blood sample. Cells of interest or suspected of being cancerous in the blood sample can be isolated or enriched according to known techniques before isolating gDNA and enriching for a gDNA subpopulation. One well known technique uses antibodies conjugated to magnetic beads or another selectable label, wherein the antibodies bind to a cell surface marker of interest. For example, B cell, T-cells, or macrophages, or another blood cell subset suspected of being cancerous can be isolated or enriched prior to isolating gDNA, e.g., using antibodies that bind to a surface antigen commonly expressed by the cell population or antibodies that bind to a known cancer-associated cell surface marker. Those of skill recognize that cancerous cells in the blood can be isolated or enriched using an antibody-based isolation or enrichment scheme. It is also possible that tissue or solid samples may be disrupted and a subpopulation isolated or enriched by antibody selection. Assessing the DNA methylation status of accessible/inaccessible DNA in a selected cell population is contemplated by the present invention.

The methods generally comprise comparing a divided biological sample, e.g., divided into a first portion and a second portion, wherein a subpopulation of genomic DNA is enriched in one of the portions. The second portion can retain total genomic DNA. Alternatively, the methods can comprise comparing two biological samples, both enriched for the same subpopulation of genomic DNA. For example, the first biological sample can be from normal tissue and the second biological sample can be from tissue suspected of being cancerous or pre-cancerous. Alternatively, the first biological sample can be treated with an agent, e.g., a chemical or pharmaceutical agent, and the second biological sample can be an untreated control sample. Preferably, in methods comparing two biological samples, both enriched for the same subpopulation of genomic DNA, the biological samples are from the same tissue type.

In various embodiments, for example where the biological sample comprises cells or tissues, the methods further comprise the step of treating the biological sample to allow the modifying agent to access the chromatin. Any treatment known in the art finds use. Illustrative treatments to apply to the cells or tissues to facilitate accessibility of chromatin to a modifying agent include without limitation, e.g., expression of the modifying agent in living cells (e.g., DamID); permeabilization of cells to allow access of the modifying agent to chromatin; isolation of cell nuclei followed by diffusion of the modifying agent into the nuclei such that it can modify chromatin; and disruption of cells to release chromatin followed by, or simultaneous with, treatment with the modifying agent.

Chromatin can be exposed to a modifying agent. The modifying agent generally preferentially modifies accessible chromatin in comparison to its ability to modify inaccessible chromatin. Any agents that modify genomic DNA find use, and those that introduce non-endogenous or non-naturally occurring modifications are more easily detected. Illustrative modifying agents include nucleases that digest DNA in accessible chromatin such that only the DNA that was in inaccessible chromatin remains. The nuclease can be any agent that digests or degrades DNA and includes chemicals, restriction enzymes and nucleases (e.g., DNase I). Additional gDNA modifying agents that find use include those that place a "mark" on the DNA in accessible chromatin. For example, the agent can be a DNA methyltransferase where the mark will be a methyl group. To analyze higher eukaryotes a DNA methyltransferase that modifies any residue that is not cytosine (e.g., adenine) can be particularly useful. Methylated adenine is not a natural base in eukaryotic cells and could thus serve as a distinguishing feature. The DAM methyltransferase is an example of an adenine methyltransferase.

3. Enriching for a Subpopulation of Genomic DNA (gDNA)

The methods evaluate the methylation status or extent or type of methylation in a subpopulation of genomic DNA. The methylation status or extent or type of methylation in the subpopulation of genomic DNA is compared to a reference, for example, total genomic DNA or genomic DNA enriched for the same subpopulation, e.g., that has been exposed to an agent or from neighboring tissue (known to be cancerous, known to be pre-cancerous, known to be non-cancerous, etc.).

Generally, the genomic DNA can enriched for accessible or inaccessible subpopulations. In some embodiments, the genomic DNA is enriched for regions in duplex with RNA. Various embodiments of the methods further include the step of enriching for histones bearing modifications specifically recognized by antibodies. Illustrative histone modifications of interest for enrichment include, e.g., Histone 3; lysine 4 mono, di and/or tri methylated Histone 3; lysine 9, mono, di and/or tri methylated Histone 3; lysine 9, acetylated Histone 3; lysine 27, mono, di and/or tri methylated Histone 3; lysine 27, acetylated Histone 3; lysine 36, mono, di and/or tri methylated Histone 3; lysine 79, mono, di and/or tri methylated Histone 4; lysine 20, mono, di and/or tri methylated acetylated Histone H3; and Acetylated Histone H4.

a. Enriching for Inaccessible gDNA

Enriching for inaccessible DNA can be accomplished by any method in the art. One method, described in U.S. application Ser. No. 12/618,076, involves simultaneous permeabilization of a cell and contacting the cell with a DNA cleaving agent under conditions such that accessible genomic DNA is cleaved, thereby enriching for inaccessible genomic DNA.

In various embodiments, inaccessible chromatin is isolated when the modifying agent is a nuclease. The nuclease treatment is such that all/most of the DNA that was in accessible chromatin is degraded leaving an enriched subpopulation of DNA that was in inaccessible chromatin. gDNA isolated from a portion of the biological sample that is not treated with the nuclease represents total DNA.

i. Permeabilizing and Disrupting Cells

Cell membranes can be permeabilized or disrupted in any way known in the art. As explained herein, the present methods involve contacting the genomic DNA prior to isolation of the DNA and thus methods of permeabilizing or disrupting the cell membrane will not disrupt the structure of the genomic DNA of the cell such that nucleosomal or chromatin structure is destroyed or perturbed.

In some embodiments, the cell membrane is contacted with an agent that permeabilizes or disrupts the cell membrane. Lysolipids are an exemplary class of agents that permeabilize cell membranes. Exemplary lysolipids include, but are not limited to, lysophosphatidylcholine (also known in the art as lysolecithin) or monopalmitoylphosphatidylcholine. A variety of lysolipids are also described in, e.g., WO 2003/052095.

Non-ionic detergents are an exemplary class of agents that disrupt cell membranes. Exemplary nonionic detergents, include but are not limited to, NP40, Tween 20 and Triton X-100.

One advantage of the present invention is the simultaneous delivery of the permeabilization agent and the DNA cleaving or DNA modifying agent. Thus, in some embodiments, a buffer comprising both agents is contacted to the cell. The buffer should be adapted for maintaining activity of both agents while maintaining the structure of the cellular chromatin.

Alternatively, electroporation or biolistic methods can be used to permeabilize a cell membrane such that a DNA modifying agent is introduced into the cell and can thus contact the genomic DNA. A wide variety of electroporation methods are well known and can be adapted for delivery of DNA modifying agents as described herein. Exemplary electroporation methods include, but are not limited to, those described in WO/2000/062855. Biolistic methods include but are not limited to those described in U.S. Pat. No. 5,179,022.

ii. Contacting with a DNA Cleaving Agent

Following permeabilization, or simultaneously with permeabilization (e.g., during electroporation or during incubation with permeabilizing agent), a DNA cleaving agent is introduced such that the agent contacts the genomic DNA, thereby introducing modifications into the DNA. A wide variety of DNA cleaving agents can be used according to the present invention.

In some embodiments, the DNA cleaving agents are contacted to the permeabilized cells following removal of the permeabilizing agent, optionally with a change of the buffer. Alternatively, in some preferred embodiments, the DNA cleaving agent is contacted to the genomic DNA without one or more intervening steps (e.g., without an exchange of buffers, washing of the cells, etc.). As noted above, this latter approach can be convenient for reducing the amount of labor and time necessary and also removes a potential source of error and contamination in the assay.

The quantity of DNA cleaving agent used, as well as the time of the reaction with the DNA cleaving agent will depend on the agent used. Those of skill in the art will appreciate how to adjust conditions depending on the agent used. Generally, the conditions of the DNA modifying step are adjusted such that a "complete" digestion is not achieved. Thus, for example, in some embodiments, the conditions of the modifying step is set such that the positive control—i.e., the control where modification is accessible and occurs—occurs at a high level but less than 100%, e.g., between 80-95%, 80-99%, 85-95%, 90-98%, etc.

Restriction Enzymes

In some embodiments, the DNA cleaving agent is a restriction enzyme. Thus, in these embodiments, the modification introduced into the genomic DNA is a sequence-specific single-stranded (e.g., a nick) or double-stranded cleavage event. A wide variety of restriction enzymes are known and can be used in the present invention.

Any type of restriction enzyme can be used. Type I enzymes cut DNA at random far from their recognition sequences. Type II enzymes cut DNA at defined positions close to or within their recognition sequences. Some Type II enzymes cleave DNA within their recognition sequences. Type II-S enzymes cleave outside of their recognition sequence to one side. The third major kind of type II enzyme, more properly referred to as "type IV," cleave outside of their recognition sequences. For example, those that recognize continuous sequences (e.g., AcuI: CTGAAG) cleave on just one side; those that recognize discontinuous sequences (e.g., BcgI: CGANNNNNNTGC) cleave on both sides releasing a small fragment containing the recognition sequence. Type III cleave outside of their recognition sequences and require two such sequences in opposite orientations within the same DNA molecule to accomplish cleavage.

The methods of the invention can be adapted for use with any type of restriction enzyme or other DNA cleaving enzyme. In some embodiments, the enzyme is one or more that cleaves relatively close (e.g., within 5, 10, or 20 base pairs) of the recognition sequence. Such enzymes can be of particular use in assaying chromatin structure as the span of DNA that must be accessible to achieve cutting is larger than the recognition sequence itself and thus may involve a wider span of DNA that is not in a "tight" chromatin structure. Sequence-specific restriction enzymes can provide improved quantitative results in part because controls based on the same DNA region can be designed as described herein (e.g., in the Examples). Thus, the number of total and digested copies can be more accurately determined compared to, e.g., digestion with sequence non-specific endonucleases ("DNases"). Illustrative enzymes that cut outside their recognition sequence includes, e.g., Type II-S, Type III, and Type IV enzymes. Type II-S restriction enzymes, include but are not limited to, MnlI, FokI and AlwI.

In some embodiments, more than one (e.g., two, three, four, etc.) restriction enzymes are used. Combinations of enzymes can involve combinations of enzymes all from one type or can be mixes of different types.

Intact or cut DNA can subsequently be separately detected and quantified and the number of intact and/or cut copies of a DNA region can be determined as described herein.

In some embodiments, the permeabilizing or membrane disrupting agent is added prior to the restriction enzyme. In some embodiments, the restriction enzyme and permeabilizing or disrupting agent are added simultaneously (e.g., in or with appropriate buffers). Even if both agents are not initially contacted to a cell at the same moment, one can still achieve simultaneous permeabilization and contact with a DNA cleaving agent because permeabilization can be an ongoing process. Thus, for example, addition of a permeabilizing agent followed soon after (before permeabilization is substantially complete) with a DNA modifying agent can be considered "simultaneously" permeabilizing and contacting the cell with the DNA modifying agent. "Simultaneous" means no intervening manipulations occur (including but not limited to change of buffer, centrifugation, etc.) between addition of the permeabilization and modifying agent.

In some embodiments, 0.5% lysolecithin (w/v), 50 mM NaCl, 10 mM Tris-HCl pH 7.4, 10 mM $MgCl_2$, 1 mM DTT, 100 µg/ml BSA and 0-500 units/ml MnlI (or other restriction enzyme) are used. In some embodiments, 0.25% lysolecithin (w/v), 50 mM NaCl, 10 mM Tris-HCl pH 7.4, 10 mM $MgCl_2$, 1 mM DTT, 100 µg/ml BSA and 0-500 units/ml MnlI (or other restriction enzyme) are used. In some embodiments, 0.75% lysolecithin (w/v), 50 mM NaCl, 10 mM Tris-HCl pH 7.4, 10 mM $MgCl_2$, 1 mM DTT, 100 µg/ml BSA and 0-500 units/ml MnlI (or other restriction enzyme) are used. In some embodiments, 1% lysolecithin (w/v), 50 mM NaCl, 10 mM Tris-HCl pH 7.4, 10 mM $MgCl_2$, 1 mM DTT, 100 µg/ml BSA and 0-800 units/ml MnlI (or other restriction enzyme) are used.

Following permeabilization and digestion, the digestion optionally is stopped and the cells are lysed, optionally by simultaneous addition of a lysis/stop buffer and/or increased temperature. Exemplary lysis/stop buffers can include sufficient chelator and detergent to stop the reaction and to lyse the cells. For example, in some embodiments, the lysis/stop buffer comprises 100 mM Tris-HCl pH 8, 100 mM NaCl, 100 mM EDTA, 5% SDS (w/v) and 3 mg/ml proteinase K. In some embodiments, the lysis/stop buffer comprises 100 mM Tris-HCl pH 8, 100 mM NaCl, 100 mM EDTA, 1% SDS (w/v) and 3 mg/ml proteinase K. In some embodiments, the lysis/stop buffer comprises 200 mM Tris-HCl pH 8, 100 mM NaCl, 500 mM EDTA, 5% SDS (w/v) and 5 mg/ml proteinase K.

DNases

In some embodiments, an enzyme that cuts or nicks DNA in a sequence non-specific manner is used as a DNA modifying agent. Thus, in some embodiments, the DNA modifying agent is a sequence non-specific endonuclease (also referred to herein as a "DNase").

Any sequence non-specific endonuclease (e.g., any of DNase I, II, III, IV, V, VI, VII) can be used according to the present invention. For example, any DNase, including but not limited to, DNase I can be used. DNases used can include naturally occurring DNases as well as modified DNases. An example of a modified DNase is TURBO DNase (Ambion), which includes mutations that allow for "hyperactivity" and salt tolerance. Exemplary DNases, include but are not limited, to Bovine Pancreatic DNase I (available from, e.g., New England Biolabs). Also of use are double strand DNases (dsDNases). One example from a dsDNase is the shrimp dsDNase, e.g., offered by Marine Biochemicals (marinebiochem.com).

Intact DNA can subsequently be separately detected and quantified and the number of intact and/or cut copies of a DNA region can be determined.

In some embodiments, the permeabilizing or membrane disrupting agent is added prior to the DNase. In some embodiments, the DNase and permeabilizing or disrupting agent are added simultaneously (e.g., with appropriate buffers). In some embodiments, the permeabilization/digestion buffer comprises 0.25% lysolecithin (w/v), 10 mM Tris-HCl pH 7.4, 2.5 mM $MgCl_2$, 0.5 mM $CaCl_2$ and 0-200 units/ml DNase I. In some embodiments, the permeabilization/digestion buffer comprises 0.5% lysolecithin (w/v), 10 mM Tris-HCl pH 7.4, 2.5 mM $MgCl_2$, 0.5 mM $CaCl_2$ and 0-200 units/ml DNase I. In some embodiments, the permeabilization/digestion buffer comprises 0.75% lysolecithin (w/v), 10 mM Tris-HCl pH 7.4, 2.5 mM $MgCl_2$, 0.5 mM $CaCl_2$ and 0-500 units/ml DNase I. In some embodiments, the permeabilization/digestion buffer comprises 0.25% lysolecithin (w/v), 10 mM Tris-HCl pH 7.4, 2.5 mM $MgCl_2$, 0.5 mM $CaCl_2$ and 0-500 units/ml DNase I. Permeabilization and lysis can be stopped, for example, as described above for restriction enzymes.

Use of a DNase or other general DNA cleaving agent can be enhanced by monitoring extent of cleavage between at least two different DNA regions, one being the target, and the other being a DNA region that is generally always accessible or is generally always inaccessible in any of the test conditions. Examples of such genes are discussed elsewhere herein and are known or can be identified. For example, DNA regions encompassing "housekeeping" genes are generally always accessible. The relative amount of remaining target compared to the control can then be used to determine relative chromatin structure at the target DNA region.

Size Selection

Inaccessible gDNA can also be enriched by size selection. gDNA fragments that were exposed to a cleaving agent can be fractionated according to size using any method in the art, including, e.g., gel filtration, electrophoresis, size exclusion, fractionation on a sucrose gradient or purification on a commercially available device such as the Pippin Prep (Sage Science, on the internet at sagescience.com) or the LabChip XT (Caliper Life Sciences, on the internet at caliperls.com). Accessible chromatin regions will be relatively smaller in size; inaccessible chromatin regions will be relatively larger. The relatively larger gDNA fragments representative of inaccessible gDNA or the relatively smaller gDNA fragments representative of accessible gDNA are used for subsequent DNA methylation determination. For example, in some embodiments, the DNA is selected for fragments larger than 100, 500, or 1000 base pairs or other sizes, including but not limited to, 500-1000 or –2000 or –3000 or –8000 base pairs.

b. Enriching for Accessible gDNA

Modifying agents that preferentially introduce non-naturally occurring modifications into the accessible gDNA find use for the enrichment of accessible gDNA. Following treatment of the biological sample with the modifying agent, the genomic DNA is isolated and can optionally be sheared into fragments. The subpopulation of DNA that was in accessible chromatin is then purified using an affinity agent that recognizes the "mark." DNA isolated from a portion of the biological sample that is not treated with modifying agent represents total DNA. Applicable methods for enriching for accessible gDNA are known in the art and find use.

DNA Modifying Agents

In methods for enriching for accessible gDNA, a DNA modifying agent is introduced into a nucleus having genomic DNA under such conditions that the DNA modifying agent modifies the genomic DNA in the nucleus such that the modification is not naturally occurring. A wide variety of DNA modifying agents can be used according to the present invention, including but not limited to enzymes, proteins, and chemicals.

In some embodiments, the DNA modifying agent is introduced into an isolated nucleus. In some embodiments, the DNA modifying agent is introduced into a nucleus in a cell following permeabilization, or simultaneously with permeabilization (e.g., during electroporation or during incubation with permeabilizing agent).

In some embodiments, the DNA modifying agents are contacted to permeabilized cells following removal of the permeabilizing agent, optionally with a change of the buffer. Alternatively, in some preferred embodiments, the DNA modifying agent is contacted to the genomic DNA without one or more intervening steps (e.g., without an exchange of buffers, washing of the cells, etc.). As noted above, this latter approach can be convenient for reducing the amount of labor and time necessary and also removes a potential source of error and contamination in the assay.

The quantity of DNA modifying agent used, as well as the time of the reaction with the DNA modifying agent will depend on the agent used. Those of skill in the art will appreciate how to adjust conditions depending on the agent used. Generally, the conditions of the DNA modifying step are adjusted such that a "complete" modification is not achieved. Thus, for example, in some embodiments, the conditions of the modifying step is set such that for the positive control—i.e., the control where modification is accessible and occurs—the number of copies of that positive control DNA region that are modified is at least about 10%, at least about 15%, 20%, 25%, 30%, 40%, or more.

Methyltransferases

In some embodiments of the invention, the DNA modifying agent generates a covalent modification to the DNA. In some embodiment, a DNA methyltransferase is used to enrich for accessible genomic DNA. A variety of methyltransferases are known in the art and find use. DNA methyltransferases covalently modify specific bases in DNA by methylating them. In mammalian genomes methylation of cytosine at the 5-position is a common epigenetic mark that is associated with gene silencing. Other types of DNA modification, such as methylation of adenine at the 6-position (6-mA), occurs in bacteria and lower eukaryotes, but is not found in mammals including humans. A DNA methyltransferase that catalyzes methylation of adenine at the 6-position could thus be used to mark mammalian chromatin with a distinguishing feature.

In some embodiments, the methyltransferase used adds a methyl moiety to adenosine in DNA. Examples of such methyltransferases include, but are not limited to, E. coli DAM methyltransferase, M.TaqI, M.EcoRV, M.Fok1, and M.EcoR1. Because adenosine generally is not methylated in eukaryotic cells, the presence of a methylated adenosine in a particular DNA region indicates that a DAM methyltransferase, M.Taq1, M.EcoRV, M.FokI, and M.EcoR1 (or other methyltransferase with similar activity) was able to access the DNA region.

In some embodiments, the methyltransferase methylates cytosines in GC sequences. Examples of such methyltransferases include, but are not limited to, M.CviP1. See, e.g., Xu et al., *Nucl. Acids Res.* 26(17): 3961-3966 (1998). Because GC sequences generally are not methylated in eukaryotic cells, the presence of a methylated GC sequence in a particular DNA region indicates that the DNA modifying agent (i.e., a methyltransferase that methylates cytosines in GC sequences) was able to access the DNA region.

In some embodiments, the methyltransferase methylates cytosines in CG (also known as "CpG") sequences. Examples of such methyltransferases include, but are not limited to, M.Sss1. Use of such methyltransferases will generally be limited to use for those DNA regions that are not typically methylated. This is because CG sequences are endogenously methylated in eukaryotic cells and thus it is not generally possible to assume that a CG sequence is methylated by the modifying agent rather than an endogenous methyltransferase except in such DNA regions where methylation is rare.

Other suitable methyltransferases that are known in the art include, for example, methyltransferases that methylate cytosine at the N4 position (e.g., M.BamHI and M.PvuI1) and methyltransferases that methylate cytosine at the C5 position (e.g., M.Hha1). Alternatively, mutated or genetically engineered methyltransferases that exhibit altered DNA target-site specificity or altered DNA modification specificity can be used.

Figure 3:
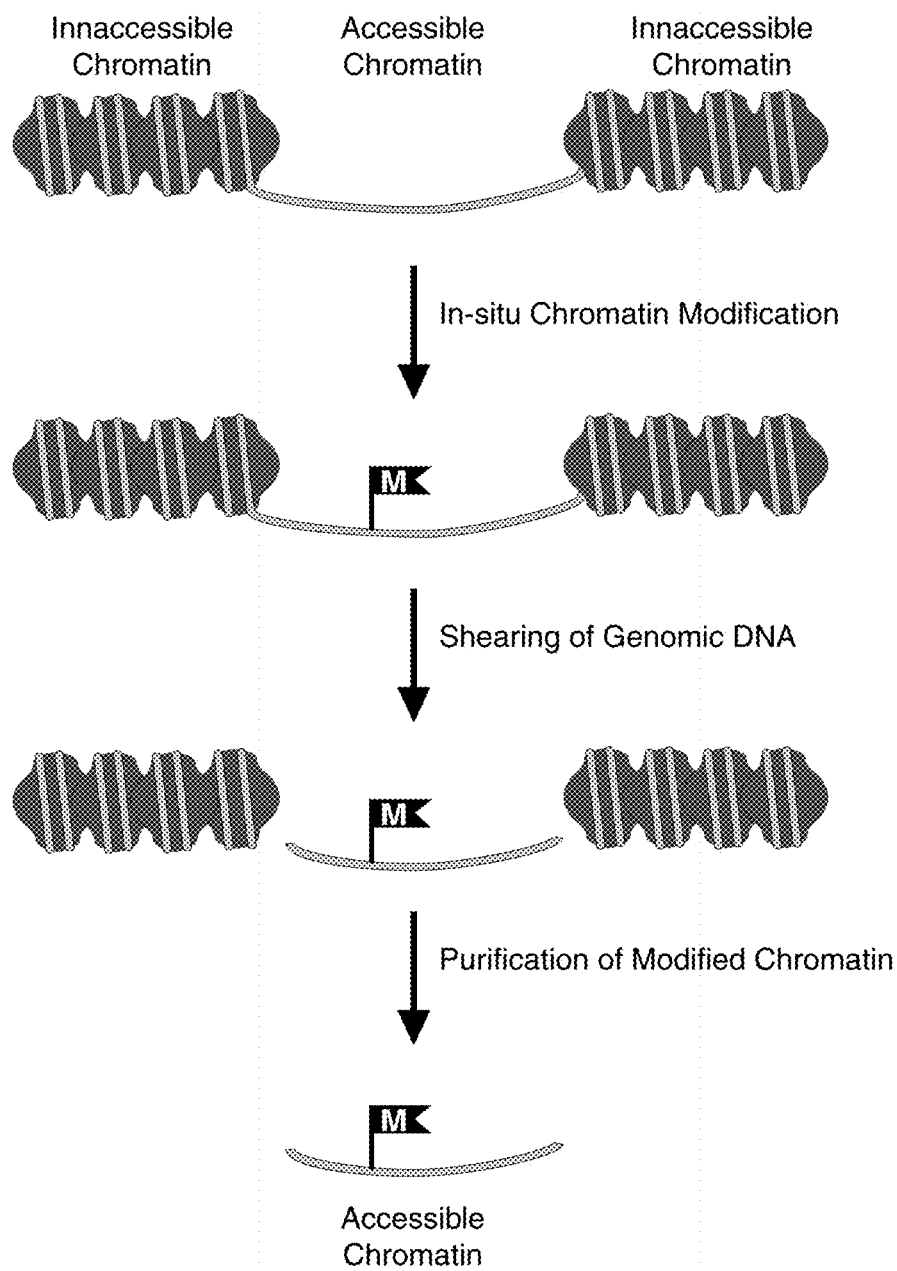
FIG. 3 illustrates a procedure for the isolation of the subpopulation of gDNA that corresponds to accessible chromatin. Permeabilized cells or isolated nuclei are treated with an agent that modifies accessible chromatin, but does not modify inaccessible chromatin. Total gDNA can be isolated and sheared into fragments of 50 bp to 1 kb or so in size. The gDNA fragments containing sites of modification are then purified by an appropriate method. The purified gDNA represents the subpopulation of gDNA that was originally in an accessible chromatin configuration.

To isolate the subpopulation of gDNA that was in accessible chromatin, a cell sample can be split into two portions. The first portion can be treated with a methyltransferase (e.g., an adenine methyltransferase) in situ to mark accessible chromatin, the second portion is not treated with the methyltransferase. gDNA can then be isolated from both cell portions and the DNA can be sheared to a constant size by any appropriate means. The gDNA from the first portion can then be subjected to affinity purification with an antibody that recognizes 6-mA. The purified gDNA represents the subpopulation of gDNA that was in an accessible chromatin structure. The second portion of gDNA is analyzed as is and represents total gDNA. See, FIG. 3.

Chemicals

In some embodiments, the DNA modifying agent comprises a DNA modifying chemical. As most DNA modifying chemicals are relatively small compared to chromatin, use of DNA modifying chemicals without a fusion partner may not be effective in some circumstances as there will be little if any difference in the extent of accessibility of different DNA regions. Therefore, in some embodiments, the DNA modifying agent comprises a molecule having steric hindrance linked to a DNA modifying chemical. The molecule having steric hindrance can be any protein or other molecule that results in differential accessibility of the DNA modifying agent depending on chromatin structure. This can be tested, for example, by comparing results to those using a methyltransferase.

In some embodiments, the molecule having steric hindrance will be at least 5, 7, 10, or 15 kD in size. Those of skill in the art will likely find it convenient to use a polypeptide as the molecule with steric hindrance. Any polypeptide can be used that does not significantly interfere with the DNA modifying agent's ability to modify DNA. In some embodiments, the polypeptide is a double-stranded sequence-non-specific nucleic acid binding domain as discussed in further detail below.

The DNA modifying chemicals of the present invention can be linked directly to the molecule having steric hindrance or via a linker. A variety of homo- and hetero-bifunctional linkers are known and can be used for this purpose.

Exemplary DNA modifying chemicals include but are not limited to hydrazine (and derivatives thereof, e.g., as described in Mathison et al., Toxicology and Applied Pharmacology 127(1):9 1-98 (1 994)) and dimethyl sulfate. In some embodiments, hydrazine introduces a methyl group to guanine in DNA or otherwise damages DNA. In some embodiments, dimethyl sulfate methylates guanine or results in the base-specific cleavage of guanine in DNA by rupturing the imidazole rings present in guanine.

DNA Binding Domains to Improve DNA Modifying Agents

In some embodiments, the DNA modifying agents used for enrichment of accessible gDNA are fused or otherwise linked to a double-stranded sequence-non-specific nucleic acid binding domain (e.g., a DNA binding domain). In cases where the DNA modifying agent is a polypeptide, the double-stranded sequence-non-specific nucleic acid binding domain can be synthesized, for example, as a protein fusion with the DNA modifying agent via recombinant DNA technology. A double-stranded sequence-non-specific nucleic acid binding domain is a protein or defined region of a protein that binds to double-stranded nucleic acid in a sequence-independent manner, i.e., binding does not exhibit a gross preference for a particular sequence. In some embodiments, double-stranded nucleic acid binding proteins exhibit a 10-fold or higher affinity for double-stranded versus single-stranded nucleic acids. The double-stranded nucleic acid binding proteins in some embodiments of the invention are thermostable. Examples of such proteins include, but are not limited to, the Archaeal small basic DNA binding proteins Sac7d and Sso7d (see, e.g., Choli et al., *Biochimica et Biophysica Acta* 950: 193-203, 1988; Baumann et al., Structural Biol. 1:808-819, 1994; and Gao et al, Nature Struc. Biol. 5:782-786, 1998), Archael HMf-like proteins (see, e.g., Starich et al., J. Molec. Biol. 255: 187-203, 1996; Sandman et al., Gene 150:207-208, 1994), and PCNA homologs (see, e.g., Cann et al., J. Bacteriology 181:6591-6599, 1999; Shamoo and Steitz, Cell: 99, 155-1 66, 1999; De Felice et al., J. Molec. Biol. 291, 47-57, 1999; and Zhang et al., Biochemistry 34:10703-10712, 1995). See also European Patent 1283875B1 for addition information regarding DNA binding domains.

Sso 7d and Sac 7d

Sso7d and Sac7d are small (about 7,000 kd MW), basic chromosomal proteins from the hyperthermophilic archaeabacteria *Sulfolobus solfataricus* and *S. acidocaldarius*, respectively. These proteins are lysine-rich and have high thermal, acid and chemical stability. They bind DNA in a sequence-independent manner and when bound, increase the T, of DNA by up to 40° C. under some conditions (McAfee et al., Biochemistry 34: 10063-10077, 1995). These proteins and their homologs are typically believed to be involved in stabilizing genomic DNA at elevated temperatures.

HMf-Like Proteins

The HMf-like proteins are archaeal histones that share homology both in amino acid sequences and in structure with eukaryotic H4 histones, which are thought to interact directly with DNA. The HMf family of proteins form stable dimers in solution, and several HMf homologs have been identified from thermostable species (e.g., *Methanothermus fervidus* and *Pyrococcus* strain GB-3a). The HMf family of proteins, once joined to Taq DNA polymerase or any DNA modifying enzyme with a low intrinsic processivity, can enhance the ability of the enzyme to slide along the DNA substrate and thus increase its processivity. For example, the dimeric HMf-like protein can be covalently linked to the N terminus of Taq DNA polymerase, e.g., via chemical modification, and thus improve the processivity of the polymerase.

Those of skill in the art will recognize that other double-stranded sequence-non-specific nucleic acid binding domains are known in the art and can also be used as described herein.

Size Selection

Modified, accessible gDNA can optionally be enriched by size selection. gDNA fragments that were exposed to a cleaving agent can be fractionated according to size using any method in the art, including, e.g., gel filtration, electrophoresis, size exclusion, fractionation on a sucrose gradient or purification on a commercially available device such as the Pippin Prep (Sage Science, on the internet at sagescience.com) or the LabChip XT (Caliper Life Sciences, on the internet at caliperls.com). Accessible chromatin regions will be relatively smaller in size; inaccessible chromatin regions will be relatively larger. The relatively larger gDNA fragments representative of inaccessible gDNA or the relatively smaller gDNA fragments representative of accessible gDNA are used for subsequent DNA methylation determination. For example, in some embodiments, the DNA is selected for fragments larger than 100, 500, or 1000 base pairs or other sizes, including but not limited to, 500-1000 or –2000 or –3000 or –8000 base pairs.

c. Isolating or Purifying Genomic DNA

Following digestion or modification of the desired subpopulation of genomic DNA, the genomic DNA (enriched and not enriched) is isolated from the cells according to any method available. Essentially any DNA purification procedure can be used so long as it results in DNA of acceptable purity for the subsequent methylation detection and quantification step(s). For example, standard cell lysis reagents can be used to lyse cells. Optionally a protease (including but not limited to proteinase K) can be used. DNA can be isolated from the mixture as is known in the art. In some embodiments, phenol/chloroform extractions are used and the DNA can be subsequently precipitated (e.g., by ethanol) and purified. In some embodiments, RNA is removed or degraded (e.g., with an RNase or with use of a DNA purification column), if desired.

4. Determining DNA Methylation Status a. Types of DNA Methylation

DNA methylation usually refers to 5-methylcytosine (5-mC) as the methylated base. However, other examples of methylated DNA bases, including 5-hydroxylmethylcytosine (5-hmC), glucosyl-5-hydroxylmethylcytosine (5-ghmC), 4-methylcytosine (4-mC) and 6-methyladenine (6-mA) exist and are included as forms of DNA methylation.

Analysis of the extent, quality and/or patterning of methylation of gDNA in a sample can be determined genome-wide, e.g., for the entirety of the gDNA in the sample (e.g., the total gDNA or subpopulation of gDNA), or at one or more preselected target gDNA regions.

b. Target DNA Regions

A gDNA region is a target sequence of interest within genomic DNA. Any gDNA sequence in genomic DNA of a cell can be evaluated for gDNA methylation status. gDNA regions can be screened to identify a DNA region of interest that displays different accessibility in different cell types, between untreated cells and cells exposed to a drug, chemical or environmental stimulus, or between normal and diseased tissue, for example. Thus, in some embodiments, the methods of the invention are used to identify a DNA region whose change in accessibility acts as a marker for disease (or lack thereof). Exemplary diseases include but are not limited to cancers. A number of genes have been described that have altered DNA methylation and/or chromatin structure in cancer cells compared to non-cancer cells. In some embodiments, the DNA region is known to be differentially accessible depending on the disease or developmental state of a particular cell.

A variety of DNA regions can be detected either for research purposes and/or as a control DNA region to confirm that the reagents perform as expected. For example, in some embodiments, a DNA region is assayed that is accessible in essentially all cells of an animal. Such DNA regions are useful, for example, as positive controls for accessibility. Such DNA regions can be found, for example, within or adjacent to genes that are constitutive or nearly constitutive. Such genes include those generally referred to as "housekeeping" genes, i.e., genes whose expression are required to maintain basic cellular function. Examples of such genes include, but are not limited to glyceraldehyde-3-phosphate dehydrogenase (GAPDH) and beta actin (ACTB). DNA regions can include all or a portion of such genes, optionally including at least a portion of the promoter.

In some embodiments, a DNA region comprises at least a portion of DNA that is inaccessible in most cells of an animal. Such DNA regions are useful, for example, as negative controls for accessibility or positive controls for inaccessibility. "Inaccessible" in this context refers to DNA regions whose copies are modified in no more than around 20% of the copies of the DNA region. Examples of such gene sequences include those generally recognized as "heterochromatic" and include genes that are only expressed in very specific cell types (e.g., expressed in a tissue or organ-specific fashion). Exemplary genes that are generally inaccessible (with the exception of specific cell types) include, but are not limited to, hemoglobin-beta chain (HBB) and immunoglobulin light chain kappa (IGK).

In some embodiments, the DNA region is a gene sequence which has different accessibility depending on the disease state of the cell or otherwise have variable accessibility depending on type of cells or growth environment. For example, some genes are generally inaccessible in non-cancer cells but are accessible in cancer cells. Examples of genes with variable accessibility include, e.g., Glutathione-s-transferase pi (GSTP1).

In some embodiments, a DNA region of the invention is selected from a gene sequence (e.g., a promoter sequence) from one or more of the following genes cadherin 1 type 1 (E-Cadherin), Cytochrome P450-1A1 (CYP1A1), Ras association domain family 1A (RASSF1A), p15, p16, Death associated protein kinase 1 (DAPK), Adenomatous Polyposis Of The Colon (APC), Methylguanine-DNA Methyltransferase (MGMT), Breast Cancer 1 Gene (BRCA1) and hMLH.

In some embodiments, the DNA regions are selected at random, for example, to identify regions that have differential accessibility between different cell types, different conditions, normal vs. diseased cells, etc.

Detection of methylation status can be performed using any method known in the art. General methods for methylation detection include without limitation use of restriction enzymes with activity governed by methylation status, use of antibodies specific for methylated nucleotide bases, polynucleotide sequencing and chemical modification of methylated nucleotide bases, e.g., such as bisulfite treatment.

c. Restriction-Enzyme Analysis

Restriction enzymes that recognize or are sensitive to methylation find use to assess the presence or absence DNA methylation in genomic DNA. One can use a methylation-sensing restriction enzyme or other methylation sensing agent to cleave DNA in either a methylation-dependent or methylation-sensitive manner. Exemplary methylation-sensitive restriction enzymes (i.e., enzymes that cut DNA if methylation is absent) include, e.g., cytosine-methylation sensitive restriction enzymes and adenosine-methylation sensitive restriction enzymes. Exemplary methylation-sensitive restriction enzymes (i.e., enzymes that cut DNA if methylation is absent) include, e.g., cytosine-methylation sensitive restriction enzymes (e.g., AatII, AciI, AclI, AgeI, AluI, AscI, AseI, AsiSI, BbeI, BsaAI, BsaHI, BsiEI, BsiWI, BsrFI, BssHII, BssKI, BstBI, BstNI, BstUI, ClaI, EaeI, EagI, FauI, FseI, HhaI, HinP1I, HinCII, HpaII, Hpy99I, HpyCH4IV, KasI, MboI, MluI, MapA1I, MspI, NaeI, NarI, No I, PmlI, PstI, Pv I, RsrII, SacII, SapI, Sau3AI, SflI, SfoI, SgrAI, SmaI, SnaBI, TscI, XmaI, and ZraI.) and adenosine-methylation sensitive restriction enzymes (e.g., DpnII). Exemplary methylation-dependent restriction enzymes (i.e., enzymes that cut DNA if methylation is present) include, e.g., cytosine-methylation dependent restriction enzymes (e.g., McrBC, GlaI and BlsI) and adenosine-methylation dependent restriction enzymes (e.g., DpnI). Analysis with DNA methylation sensing restriction enzymes is described, e.g., in Holemon et al, *BioTechniques*, (2007) 43:683-693).

DNA methylation usually refers to 5-methylcytosine (5-mC) as the methylated base. However, other examples of methylated DNA bases exist, including without limitation 5-hydroxylmethylcytosine (5-hmC), glucosyl-5-hydroxylmethylcytosine (5-ghmC), 4-methylcytosine (4-mC) and 6-methyladenine (6-mA) and are contemplated herein as forms of DNA methylation. 5-hmC and 5-ghmC can be analyzed by treatment of the gDNA in the biological samples with a glucosyltransferase, e.g., T4 phage β-glucosyltransferase.

Kits for methylation detection using enzymatic analysis are commercially available, e.g., from SABiosciences (sabiosciences.com), New England Biolabs (neb.com) and Zymo Research (zymoresearch.com). Assays that detect alternate methylated bases include the EpiMark 5-hmC and 5-mC Analysis Kit (New England Biolabs), the Quest 5-hmC Detection Kit (Zymo Research) and the restriction enzyme DpnI (New England Biolabs) which only digests DNA that contains 6-mA.

d. Affinity-Based Analysis

Antibodies that recognize or are sensitive to methylated bases are available and find use to assess the presence or absence DNA methylation in genomic DNA. Methylated DNA immunoprecipitation (MeDIP or mDIP) is a chromosome- or genome-wide technique that can be used to enrich for methylated DNA sequences. Methylated DNA fragments of about 300-1000 base pairs (bp) in length can be isolated via an antibody raised against 5-methylcytosine (5mC). See, Weber, et al., *Nat. Genet.* (2007) 37 (8): 853-62. The purified fraction of methylated DNA can be input to high-throughput DNA detection methods such as high-resolution DNA microarrays (MeDIP-chip) or next-generation sequencing (MeDIP-seq). See, Down, et al., *Nat. Biotechnol.* (2008) 26 (7): 779-85 and Jacinto, et al., *BioTechniques* (2008) 44 (1): 35-39. MeDIP assays, in combination with hybridization on high-resolution microarrays or high-throughput sequencing (HTS) techniques, find use for identifying methylated CpG-rich sequences. Antibodies against 5-methyl cytidine are commercially available, e.g., from Eurogentec (eurogentec.com), Abcam (abcam.com), and Diagenode, and find use to immunoprecipitate methylated DNA fragments.

In various embodiments, methyl-CpG binding domain proteins (MBD) are used in methylation analysis. For example, histidine-tagged MBD2b/MBD3L1 protein complexes are available in kits for enrichment of methylated gDNA (e.g., MethylCollector™ Ultra kit from Active Motif). The MBD protein may also be conjugated to a detectable label, e.g., a fluorophore or a fluorescing protein, for direct detection of methylation. See, e.g., Yu, et al., *Anal Chem.* (2010) 82(12):5012-9. Antibodies against MBD proteins may also be used to immunoprecipitate regions of gDNA bound by the MBD protein. Antibodies against MBD1, MBD2, MBD3, MBD4, MBD5, MBD6, MBD7 and other MBD variants and isoforms find use and are known in the art. For example, monoclonal antibodies against MBD1 are available from, e.g., Active Motif (activemotif.com), Millipore (millepore.com), Aviva Systems Biology (avivasysbio.com) and Cayman Chemical (caymanchem.com). Antibodies against MBD2 are available from, e.g., Cayman Chemical, USCN Life Science (uscnk.com), Abcam (abcam.com) and Epigentek (epigentek.com). Antibodies against MBD3 are available from, e.g., Active Motif, Abcam, Cell Signaling Technology (cellsignal.com) and Abgent (abgent.com). Antibodies against MBD4 are available from, e.g., Active Motif, Abcam, Abnova Corp. (abnova.com), Sigma-Aldrich (sigmaaldrich.com), Santa Cruz Biotechnology (scbt.com) and Diagenode (diagenode.com). Antibodies against MBD5 are available from, e.g., Antibodies-online (antibodies-online.com), Abcam, Santa Cruz Biotechnology and Novus Biologicals (novusbio.com). Antibodies against MBD6 are available from, e.g., Sigma Aldrich and Abcam.

Antibodies against 5-methyl cytidine or one or more MBD protein variants can be used alone or in combination. Generally, genomic DNA is extracted from the cells and purified using any method in the art. The purified DNA is cleaved into smaller fragments, using any appropriate methods, including, e.g., enzymatic cleavage or mechanical shearing, e.g., sonication. The resulting fragments preferably are in the range of from 300 to 1000 base pairs (bp) in length. In various embodiments, the DNA fragments can optionally be denatured to produce single-stranded DNA. The DNA is then incubated with antibodies against 5-methyl cytidine or one or more MBD protein variants. Immunoprecipitation techniques known in the art are then applied to enrich for DNA fragments containing target antigen (i.e., 5-methyl cytidine and/or one or more MBD protein variants), and separate from unbound DNA washed away with the supernatant. DNA can be removed from the bound antibody using any method known in the art. In various embodiments, a protease can be used to release the bound DNA. For example, proteinase K finds use to digest the antibodies and release the DNA. The immunoprecipitated and released DNA can then be collected and prepared for quantification of the extent, quality and/or patterning of methylation, as described herein. See, e.g., Weber, et al., supra; Pomraning et al., Methods (2009) 47 (3): 142-50; Wilson et al., *Cell Cycle* (2005) 5: 155-8; and Zhang, et al. Cell (2006) 126 (6): 1189-201.

e. Polynucleotide Sequencing

A variety of methods can be used to determine the nucleotide sequence and the extent to which sequenced nucleotides are modified, e.g., methylated. Any sequencing method known in the art can be used so long as it can simultaneously determine the nucleotide sequence and whether sequenced nucleotides are modified, e.g., methylated. As used herein, "simultaneously" means that as the sequencing process determines the order of nucleotides in a nucleic acid fragment, at the same time it can also distinguish between modified nucleotides (e.g., methylated nucleotides) and nonmodified nucleotides (e.g., non-methylated nucleotides). Examples of sequencing processes that can simultaneous detect nucleotide sequence and distinguish whether sequenced nucleotides are modified include, but are not limited to, single-molecule real-time (SMRT) sequencing and nanopore sequencing.

In some embodiments, nucleotide sequencing comprises template-dependent replication of the DNA region that results in incorporation of labeled nucleotides (e.g., fluorescently labeled nucleotides), and wherein an arrival time and/or duration of an interval between signal generated from different incorporated nucleotides is determinative of the presence or absence of the modification and/or the identity of an incorporated nucleotide.

i. Single-Molecule Real-Time ("SMRT") Sequencing

In some embodiments, genomic DNA comprising a target DNA region is sequenced by single-molecule, real-time (SMRT) sequencing. SMRT sequencing is a process by which single DNA polymerase molecules are observed in real time while they catalyze the incorporation of fluorescently labeled nucleotides complementary to a template nucleic acid strand. Methods of SMRT sequencing are known in the art and were initially described by Flusberg et al., Nature Methods, 7:461-465 (2010), which is incorporated herein by reference for all purposes.

Briefly, in SMRT sequencing, incorporation of a nucleotide is detected as a pulse of fluorescence whose color identifies that nucleotide. The pulse ends when the fluorophore, which is linked to the nucleotide's terminal phosphate, is cleaved by the polymerase before the polymerase translocates to the next base in the DNA template. Fluorescence pulses are characterized by emission spectra as well as by the duration of the pulse ("pulse width") and the interval between successive pulses ("interpulse duration" or "IPD"). Pulse width is a function of all kinetic steps after nucleotide binding and up to fluorophore release, and IPD is a function of the kinetics of nucleotide binding and polymerase translocation. Thus, DNA polymerase kinetics can be monitored by measuring the fluorescence pulses in SMRT sequencing.

In addition to measuring differences in fluorescence pulse characteristics for each fluorescently-labeled nucleotide (i.e., adenine, guanine, thymine, and cytosine), differences can also be measured for non-methylated versus methylated bases. For example, the presence of a methylated base alters the IPD of the methylated base as compared to its non-methylated counterpart (e.g., methylated cytosine or adenine as compared to non-methylated cytosine or adenine). Additionally, the presence of a methylated base alters the pulse width of the methylated base as compared to its non-methylated counterpart (e.g., methylated cytosine or adenine as compared to nonmethylated cytosine or adenine) and furthermore, different modifications have different pulse widths (e.g., 5-hydroxymethylcytosine has a more pronounced excursion than 5-methylcytosine). Thus, each type of non-modified base and modified base has a unique signature based on its combination of IPD and pulse width in a given context. The sensitivity of SMRT sequencing can be further enhanced by optimizing solution conditions, polymerase mutations and algorithmic approaches that take advantage of the nucleotides' kinetic signatures, and deconvolution techniques to help resolve neighboring methylcytosine bases.

ii. Nanopore Sequencing

In some embodiments, nucleotide sequencing does not comprise template-dependent replication of a DNA region. In some embodiments, genomic DNA comprising a target DNA region is sequenced by nanopore sequencing. Nanopore sequencing is a process by which a polynucleotide or nucleic acid fragment is passed through a pore (such as a protein pore) under an applied potential while recording modulations of the ionic current passing through the pore. Methods of nanopore sequencing are known in the art; see, e.g., Clarke et al., Nature Nanotechnology 4:265-270 (2009), which is incorporated herein by reference for all purposes.

Briefly, in nanopore sequencing, as a single-stranded DNA molecule passes through a protein pore, each base is registered, in sequence, by a characteristic decrease in current amplitude which results from the extent to which each base blocks the pore. An individual nucleobase can be identified on a static strand, and by sufficiently slowing the rate of speed of the DNA translocation (e.g., through the use of enzymes) or improving the rate of DNA capture by the pore (e.g., by mutating key residues within the protein pore), an individual nucleobase can also be identified while moving.

In some embodiments, nanopore sequencing comprises the use of an exonuclease to liberate individual nucleotides from a strand of DNA, wherein the bases are identified in order of release, and the use of an adaptor molecule that is covalently attached to the pore in order to permit continuous base detection as the DNA molecule moves through the pore. As the nucleotide passes through the pore, it is characterized by a signature residual current and a signature dwell time within the adapter, making it possible to discriminate between nonmethylated. Additionally, different dwell times are seen between methylated nucleotides and the corresponding non-methylated nucleotides (e.g., 5-methyl-dCMP has a longer dwell time than dCMP), thus making it possible to simultaneously determine nucleotide sequence and whether sequenced nucleotides are modified. The sensitivity of nanopore sequencing can be further enhanced by optimizing salt concentrations, adjusting the applied potential, pH, and temperature, or mutating the exonuclease to vary its rate of processivity.

f. Bisulfite Modification

In some embodiments, bisulfite modification is used to determine the extent of methylation. Bisulfite modification is a preliminary step. In bisulfite modification, the DNA is contacted with bisulfite, thereby converting unmethylated cytosines to uracils in the DNA. The methylation of a particular DNA region can then be determined by any number of methylation detection methods. In some embodiments, a high resolution melt assay (HRM) can be employed to detect methylation status following bisulfite conversion. In this method, a DNA region is amplified following bisulfite conversion and the resulting amplicon's melting temperature is determined. Because the melting temperature will differ depending on whether the cytosines were converted by bisulfite (and subsequently copied as "T"s in the amplification reaction), melting temperature of the amplicon can be correlated to methylation content. Bisulfite-based methods for detecting methylation are described, e.g., in Kristensen et al., *Clin. Chem.* (2009) 55:471-1483. Any method known in the art can be used to assess DNA methylation of bisulfite modified DNA, including without limitation, e.g., MSP, bisulfite sequencing, heavy methyl COBRA. Applicable techniques are described, e.g., in Laird, *Nat Rev Cancer.* (2003) 3(4):253-66; Laird, *Hum Mol Genet.* (2005) 14 Spec No 1:R65-76; and Cottrell and Laird, *Ann N Y Acad Sci.* (2003) 983:120-30.

Commercial bisulfite conversion kits are readily available and include the MethylDetector™ Bisulfite Modification Kit from ActiveMotif (activemotif.com), the DNA Methylation Detection Kit from BioChain (biochain.com), Life Technologies' MethylCode Bisulfite Conversion Kit (lifetechnologies.com; appliedbiosystems.com), Millipore's CpGenome Fast DNA Modification Kit (millepore.com), Qiagen's EpiTect Bisulfite Kits (qiagen.com), and Zymo Research's EZ DNA Methylation™ kits.

5. Chromatin Immunoprecipitation (ChIP) and Determining Histone Modification Status In various embodiments, the methods further comprise assessing the DNA methylation status of a subpopulation of gDNA that was originally associated with a particular histone type, hi stone modification or a particular protein. This can be conveniently accomplished using Chromatin Immunoprecipitation (ChIP). ChIP can be used to investigate the interaction between proteins and genomic DNA. ChIP finds use to determine whether specific proteins are associated with specific genomic regions, such as transcription factors on promoters or other DNA binding sites. ChIP also finds use to determine specific locations in the genome that various histone modifications are associated with, indicating the target of the histone modifiers. See, e.g., Collas, et al., *Mol Biotechnol.* (2010) 45(1):87-100; Acevedo, et al., *Biotechniques* (2007) 43(6):791-7; Oberley, et al., *Methods Enzymol* (2004) 376:315-34; Birney, et al, *Nature* (2007) 447(7146):799-816; O'Geen, et al., *BioTechniques* (2006) 41(5). Detailed protocols for performing ChIP are available online, e.g., at farnham.genomecenter.ucdavis.edu/protocol.html, and find use. Differences in histone modification or proteins associated with a DNA subpopulation relative to total DNA can have scientific, biological, clinical, physiological or pathological relevance. The procedure to determine such information varies according to the DNA subpopulation analyzed.

Generally, in performing ChIP, protein with chromatin in a cell lysate is temporarily bonded, the DNA-protein complexes (chromatin-protein) are then sheared and DNA fragments associated with the protein(s) of interest are selectively immunoprecipitated. In various embodiments, the DNA-protein complexes are reversibly cross-linked, e.g., using UV light or formaldehyde, prior to immunoprecipitation. The cross-linked chromatin can be sheared into fragments of about 300-1000 base pairs (bp) in length, e.g., using any appropriate methods, including, e.g., enzymatic cleavage or mechanical shearing, e.g., sonication. In other embodiments, the chromatin-protein complexes are not cross-linked. Instead, the chromatin is subject to micrococcal nuclease digestion, which cuts DNA at the length of the linker, leaving nucleosomes intact. Chromatin fragments of about 400-500 bp cover two to three nucleosomes. Protein-DNA complexes are selectively immunoprecipitated using known techniques and antibodies that specifically bind to the protein(s) of interest. The immunoprecipitated complexes are then collected and washed to remove non-specifically bound chromatin, the protein-DNA cross-link is reversed, and proteins are released from the bound DNA, e.g., using a protease. The immunoprecipitated DNA associated with the complex is then purified and the extent, quality and/or patterning of DNA methylation and DNA sequences are determined using any method, including those described herein.

Analysis of histone modifications and/or histone proteins can be performed on gDNA that has been enriched for inaccessible or accessible chromatin. In accordance with the present methods, ChIP allows for further enrichment of a subpopulation of gDNA (either inaccessible or accessible) that is associated with a particular protein or histone modification. The DNA methylation status of the subpopulation, e.g., versus a control population (treated or untreated) or the total gDNA population.

Accordingly, various embodiments of the methods further include the step of enriching for histones bearing modifications specifically recognized by antibodies. Illustrative histone modifications of interest for enrichment include, e.g., Histone 3; lysine 4 mono, di and/or tri methylated Histone 3; lysine 9, mono, di and/or tri methylated Histone 3; lysine 9, acetylated Histone 3; lysine 27, mono, di and/or tri methylated Histone 3; lysine 27, acetylated Histone 3; lysine 36, mono, di and/or tri methylated Histone 3; lysine 79, mono, di and/or tri methylated Histone 4; lysine 20, mono, di and/or tri methylated acetylated Histone H3; and Acetylated Histone H4.

Numerous chromatin immunoprepitation kits are commercially available and find use. Illustrative kits are available from, e.g., Sigma Aldrich (sigmaaldrich.com), Active Motif (activemotif.com), Millepore (millepore.com), Thermo Scientific (piercenet.com), R&D Systems (rndsystems.com), Imgenex (imgenex.com) and Epigentek (epigentek.com).

6. Quantifying the Extent, Quality and/or Patterning of Methylation

The invention provides for comparison with a reference the extent, or quality or patterning of methylation of a subpopulation of genomic DNA. The reference can be total genomic DNA or genomic DNA enriched for the same subpopulation in a control. Depending on the test sample, the control sample may be treated or untreated with an agent, e.g., a pharmacological agent or drug. In other embodiments, depending on the test sample, the control sample may be cancerous, pre-cancerous or non-cancerous.

The determination of the extent, quality or patterning of methylation can be genome-wide, e.g., with respect to the entirety of the genomic DNA in the sample being tested, or can be made with reference to a particular region of genomic DNA. As needed or desired, the determination of the extent, quality or patterning of methylation can be target specific (e.g., to one or more particular gDNA regions) or non-target specific. In various embodiments, the extent, quality or patterning of methylation of a first DNA region is compared with a second DNA region in a cell's genome. Alternatively, or in addition, the extent, quality or patterning of methylation of the same DNA region is compared in two different genomic DNA samples, e.g., the subpopulation and control reference. The genomic DNA samples can be from the same or a different cell population. For example, the two cells can represent diseased and healthy cells or tissues, different cell types, different stages of development (including but not limited to stem cells or progenitor cells), etc. Thus, by using the methods of the invention one can detect differences in methylation extent, quality or patterning between cells and/or determine relative methylation characteristics between two or more DNA regions (e.g., genes) within one cell. In addition, one can determine the effect of a drug, chemical or environmental stimulus on the chromatin structure/DNA methylation status of a particular region in the same cells or in different cells.

In some embodiments, a difference comprises a 10%, 20%, 25%, 30%, 50%, 75%, 100%, or greater, increase in the extent of methylation in the subpopulation of gDNA in comparison to the gDNA control. In some embodiments, a difference comprises a 10%, 20%, 25%, 30%, 50%, 75%, 100%, or greater, decrease in the extent of methylation in the subpopulation of gDNA in comparison to the gDNA control. In some embodiments, the extent of methylation between the subpopulation gDNA and control gDNA will be approximately the same, but the quality and/or patterning of the methylation will be detectably different.

The method for quantifying the extent, quality or patterning of methylation will depend on the enriched gDNA subpopulation and method used for determining methylation. In some embodiments, methylation can be detected and quantified using sequence techniques as described above. For example, all or a representative number of copies of sequences in the sample can be sequenced thereby providing quantity and sequence information for an enriched class of polynucleotides. In some embodiments, the sequencing can simultaneously determine methylation, also as described above.

In some embodiments, the enriched DNA is hybridized to one or more nucleic acids. In some embodiments, the nucleic acids are linked to a solid support, e.g., a microarray or beads. These embodiments are of particular use for genome-wide analyses as multiple enriched sequences can be simultaneously hybridized to the microarray and hybridization can subsequently be detected and quantified. See, e.g., Nimblegen™ Sequence Capture technology. In some of the embodiments described herein, nucleic acid adaptors are ligated or otherwise linked to the enriched DNA, thereby allowing for convenient amplification and/or sequencing of the enriched DNA.

In other embodiments, double stranded DNA cleavage events (e.g., as introduced by a restriction enzyme or DNase or introduced following modification, e.g., by a methylation-sensitive or -dependent restriction enzyme following methyltransferase treatment, or following modification by a DNA modifying chemical as described herein) can be conveniently detected using an amplification reaction designed to generate an amplicon that comprises a DNA region of interest. In the case of cleavage events at defined sites, such as when a sequence-specific restriction enzyme is used, primers are designed to generate an amplicon that spans a potential cleavage site. Only intact DNA will be amplified. If one also knows the amount of total DNA, one can calculate the amount of cleaved DNA as the difference between total and intact DNA. The total amount of DNA can be determined according to any method of DNA quantification known in the art. In some embodiments, the amount of total DNA can be conveniently determined by designing a set of primers that amplify the DNA regardless of modification. This can be achieved, for example, by designing primers that do not span a potential cleavage site, either within the same gene region or in another DNA region. In the case of cleavage events at indeterminate sites, such as when a non-sequence-specific nuclease, such as DNase I is used, the use of an inaccessible reference gene should be incorporated as an internal control.

As discussed in more detail below, quantitative amplification (including, for example real-time PCR) methods allow for determination of the amount of intact copies of a DNA region, and when used with various controls can be used to determine the relative amount of intact DNA compared to the total number of copies in the cell. The actual or relative number (e.g., relative to the total number of copies or relative to the number of modified or cleaved or unmodified or uncleaved copies of a second DNA region) of modified or unmodified copies of the DNA region can thus be calculated.

In some embodiments of the invention, the number of modified copies of a DNA region are determined directly following enrichment for cleaved or uncleaved DNA. For example, restriction enzyme cleavage can be detected and quantified, for example, by detecting specific ligation events, for example, that will occur only in the presence of specific sticky or blunt ends. For example, nucleic acid adaptors comprising sticky ends that are complementary to sticky ends generated by a restriction enzyme can be ligated to the cleaved genomic DNA. The number of ligation events can then be detected and quantified (e.g., by a quantitative amplification method).

In some embodiments, ligation mediated PCR (LM-PCR) is employed to quantify the number of cleaved copies of a DNA region. Methods of LM-PCR are known in the art and were initially described in Pfeifer et al., Science 246: 810-813 (1989). LM-PCR can be performed in real-time for quantitative results if desired.

Quantitative amplification methods (e.g., quantitative PCR or quantitative linear amplification) involve amplification of an nucleic acid template, directly or indirectly (e.g., determining a Ct value) determining the amount of amplified DNA, and then calculating the amount of initial template based on the number of cycles of the amplification. Amplification of a DNA locus using reactions is well known (see U.S. Pat. Nos. 4,683,195 and 4,683,202; PCR PROTO- COLS: A GUIDE TO METHODS AND APPLICATIONS (Innis et al., eds, 1990)). Typically, PCR is used to amplify DNA templates. However, alternative methods of amplification have been described and can also be employed, as long as the alternative methods amplify intact DNA to a greater extent than the methods amplify cleaved DNA. Methods of quantitative amplification are disclosed in, e.g., U.S. Pat. Nos. 6,180,349; 6,033,854; and 5,972,602, as well as in, e.g., Gibson et al., *Genome Research* 6:995-1001 (1996); DeGraves, et al., *Biotechniques* 34(1):106-10, 112-5 (2003); Deiman B, et al., *Mol Biotechnol.* 20(2):163-79 (2002). Amplifications can be monitored in "real time."

In some embodiments, quantitative amplification is based on the monitoring of the signal (e.g., fluorescence of a probe) representing copies of the template in cycles of an amplification (e.g., PCR) reaction. In the initial cycles of the PCR, a very low signal is observed because the quantity of the amplicon formed does not support a measurable signal output from the assay. After the initial cycles, as the amount of formed amplicon increases, the signal intensity increases to a measurable level and reaches a plateau in later cycles when the PCR enters into a non-logarithmic phase. Through a plot of the signal intensity versus the cycle number, the specific cycle at which a measurable signal is obtained from the PCR reaction can be deduced and used to back-calculate the quantity of the target before the start of the PCR. The number of the specific cycles that is determined by this method is typically referred to as the cycle threshold (Ct). Illustrative methods are described in, e.g., Heid et al. *Genome Methods* 6:986-94 (1996) with reference to hydrolysis probes.

One method for detection of amplification products is the 5'-3' exonuclease "hydrolysis" PCR assay (also referred to as the TaqMan™ assay) (U.S. Pat. Nos. 5,210,015 and 5,487,972; Holland et al., *Proc Natl Acad Sci USA* 88: 7276-7280 (1991); Lee et al., *Nucleic Acids Res.* 21: 3761-3766 (1993)). This assay detects the accumulation of a specific PCR product by hybridization and cleavage of a doubly labeled fluorogenic probe (the "TaqMan™ probe) during the amplification reaction. The fluorogenic probe consists of an oligonucleotide labeled with both a fluorescent reporter dye and a quencher dye. During PCR, this probe is cleaved by the 5'-exonuclease activity of DNA polymerase if, and only if, it hybridizes to the segment being amplified. Cleavage of the probe generates an increase in the fluorescence intensity of the reporter dye.

Another method of detecting amplification products that relies on the use of energy transfer is the "beacon probe" method described by Tyagi and Kramer, *Nature Biotech.* 14:303-309 (1996), which is also the subject of U.S. Pat. Nos. 5,119,801 and 5,312,728. This method employs oligonucleotide hybridization probes that can form hairpin structures. On one end of the hybridization probe (either the 5' or 3' end), there is a donor fluorophore, and on the other end, an acceptor moiety. In the case of the Tyagi and Kramer method, this acceptor moiety is a quencher, that is, the acceptor absorbs energy released by the donor, but then does not itself fluoresce. Thus, when the beacon is in the open conformation, the fluorescence of the donor fluorophore is detectable, whereas when the beacon is in hairpin (closed) conformation, the fluorescence of the donor fluorophore is quenched. When employed in PCR, the molecular beacon probe, which hybridizes to one of the strands of the PCR product, is in the open conformation and fluorescence is detected, while those that remain unhybridized will not fluoresce (Tyagi and Kramer, *Nature Biotechnol.* 14: 303-306 (1996)). As a result, the amount of fluorescence will increase as the amount of PCR product increases, and thus may be used as a measure of the progress of the PCR. Those of skill in the art will recognize that other methods of quantitative amplification are also available.

Various other techniques for performing quantitative amplification of a nucleic acids are also known. For example, some methodologies employ one or more probe oligonucleotides that are structured such that a change in fluorescence is generated when the oligonucleotide(s) is hybridized to a target nucleic acid. For example, one such method involves is a dual fluorophore approach that exploits fluorescence resonance energy transfer (FRET), e.g., Light-Cycler™ hybridization probes, where two oligo probes anneal to the amplicon. The oligonucleotides are designed to hybridize in a head-to-tail orientation with the fluorophores separated at a distance that is compatible with efficient energy transfer. Other examples of labeled oligonucleotides that are structured to emit a signal when bound to a nucleic acid or incorporated into an extension product include: Scorpions™ probes (e.g., Whitcombe et al., Nature Biotechnology 17:804-807, 1999, and U.S. Pat. No. 6,326,145), Sunrise™ (or Amplifluor™) probes (e.g., Nazarenko et al., *Nuc. Acids Res.* 25:2516-2521, 1997, and U.S. Pat. No. 6,117,635), and probes that form a secondary structure that results in reduced signal without a quencher and that emits increased signal when hybridized to a target (e.g., Lux Probes™).

In other embodiments, intercalating agents that produce a signal when intercalated in double stranded DNA may be used. Exemplary agents include SYBR GREEN™, SYBR GOLD™, and EVAGREEN™. Since these agents are not template-specific, it is assumed that the signal is generated based on template-specific amplification. This can be confirmed by monitoring signal as a function of temperature because melting point of template sequences will generally be much higher than, for example, primer-dimers, etc.

In some embodiments, the quantity of a DNA region is determined by nucleotide sequencing copies in a sample and then determining the relative or absolute number of copies having the same sequence in a sample.

Quantification of cleaved or modified (or unmodified or uncleaved) DNA regions according to the method of the invention can be further improved, in some embodiments, by determining the relative amount (e.g., a normalized value such as a ratio or percentage) of cleaved or modified or unmodified or uncleaved copies of the DNA region compared to the total number of copies of that same region. In some embodiments, the relative amount of cleaved or modified or unmodified or uncleaved copies of one DNA region is compared to the number of cleaved or modified or unmodified or uncleaved copies of a second (or more) DNA regions. In some embodiments, when comparing between two or more DNA regions, the relative amount of cleaved or modified or unmodified or uncleaved copies of each DNA region can be first normalized to the total number of copies of the DNA region. Alternatively, when obtained from the same sample, in some embodiments, one can assume that the total number of copies of each DNA region is roughly the same and therefore, when comparing between two or more DNA regions, the relative amount (e.g., the ratio or percentage) of cleaved or modified or unmodified or uncleaved copies between each DNA region is determined without first normalizing each value to the total number of copies.

In some embodiments, the actual or relative (e.g., relative to total DNA) amount of cleaved or modified or unmodified or uncleaved copies is compared to a control value. Control values can be conveniently used, for example, where one wants to know whether the accessibility of a particular DNA region exceeds or is under a particular value. For example, in the situation where a particular DNA region is typically accessible in normal cells, but is inaccessible in diseased cells (or vice versa), one may simply compare the actual or relative number of cleaved or modified or unmodified or uncleaved copies to a control value (e.g., greater or less than 20% modified or unmodified, greater or less than 80% modified or unmodified, etc.). Alternatively, a control value can represent past or expected data regarding a control DNA region. In these cases, the actual or relative amount of a control DNA region are determined (optionally for a number of times) and the resulting data is used to generate a control value that can be compared with actual or relative number of cleaved or modified or unmodified or uncleaved copies determined for a DNA region of interest.

The calculations for the methods described herein can involve computer-based calculations and tools. The tools are advantageously provided in the form of computer programs that are executable by a general purpose computer system (referred to herein as a "host computer") of conventional design. The host computer may be configured with many different hardware components and can be made in many dimensions and styles (e.g., desktop PC, laptop, tablet PC, handheld computer, server, workstation, mainframe). Standard components, such as monitors, keyboards, disk drives, CD and/or DVD drives, and the like, may be included. Where the host computer is attached to a network, the connections may be provided via any suitable transport media (e.g., wired, optical, and/or wireless media) and any suitable communication protocol (e.g., TCPIIP); the host computer may include suitable networking hardware (e.g., modem, Ethernet card, WiFi card). The host computer may implement any of a variety of operating systems, including UNIX, Linux, Microsoft Windows, MacOS, or any other operating system.

Computer code for implementing aspects of the present invention may be written in a variety of languages, including PERL, C, C++, Java, JavaScript, VBScript, AWK, or any other scripting or programming language that can be executed on the host computer or that can be compiled to execute on the host computer. Code may also be written or distributed in low level languages such as assembler languages or machine languages.

The host computer system advantageously provides an interface via which the user controls operation of the tools. In the examples described herein, software tools are implemented as scripts (e.g., using PERL), execution of which can be initiated by a user from a standard command line interface of an operating system such as Linux or UNIX. Those skilled in the art will appreciate that commands can be adapted to the operating. system as appropriate. In other embodiments, a graphical user interface may be provided, allowing the user to control operations using a pointing device. Thus, the present invention is not limited to any particular user interface.

7. Reporting Diagnosis and/or Providing Therapy to Subject

The present methods find use as a diagnostic and/or prognostic tool. Once a diagnosis or prognosis is established using the present methods, a regimen of treatment can be established or an existing regimen of treatment can be altered in view of the diagnosis or prognosis. For instance, detection of a cancer cell according to the methods of the invention can lead to the administration of chemotherapeutic agents and/or radiation to an individual from whom the cancer cell was detected.

Accordingly, in some embodiments, the methods further comprise the step of providing a diagnosis to the patient, e.g., based on the information obtained regarding biological, pathological, genetic, epigenetic, or disease status based on information relating to extent, quality and/or patterning of methylation in the subpopulation of DNA in comparison to the control.

In some embodiments, the methods further comprise the step of recommending or providing a regimen of treatment to the patient, e.g., based on the information obtained regarding biological, pathological, genetic, epigenetic, or disease status based on information relating to extent, quality and/or patterning of methylation in the subpopulation of DNA in comparison to the control.

EXAMPLES

The following examples are offered to illustrate, but not to limit the claimed invention.

Example 1

Epigenetic Changes in a Subpopulation of Cells

The following example illustrates use of the present methods to assess a biopsy. The purpose of the experiment is to determine if a tissue biopsy sample contains a subpopulation of cells that exhibits aberrant epigenetic regulation of a specific genetic biomarker. Such results can indicate the presence of a malignancy in a background of healthy cells.

For the purposes of this example, the genetic biomarker may be a gDNA region corresponding to the promoter of a tumor suppressor gene. Aberrant epigenetic regulation of the genetic biomarker is detected if the DNA is methylated and is in a closed chromatin configuration. Such information indicates that the expression of the genetic biomarker has been inappropriately silenced, which is often associated with malignant cells.

The biopsy is first treated under a condition that dissociates the biopsy sample into a single-cell suspension. A portion of the biopsy sample is then treated with an agent that permeabilizes the cell membrane and allows entry of a nuclease. The nuclease digests accessible chromatin, but does not digest chromatin that is in an inaccessible conformation. A second portion of the biopsy is treated similarly to the first treatment, but no nuclease is added. It thus serves as a no nuclease control. Total gDNA is then isolated from both biopsy treatments, and a portion of the gDNA samples are treated with a methylation-dependent restriction enzyme (MDRE) that digests methylated DNA only.

The samples are then assessed by real-time PCR using primer sets that amplify the genetic biomarker. A list of the samples is below:

| Sample # | Nuclease treated? | MDRE treated? |
|---|---|---|
| 1 | No | No |
| 2 | No | Yes |
| 3 | Yes | No |
| 4 | Yes | Yes |

The extent of methylation of the genetic biomarker in total gDNA can be estimated by comparing samples 1 and 2. Similarly, the extent of methylation of the genetic biomarker in inaccessible chromatin can be estimated by comparing samples 3 and 4. If the extent of methylation of the genetic biomarker is significantly higher in inaccessible chromatin than in total gDNA, the results imply that the genetic biomarker is inappropriately silenced in a portion of the biopsy suggestive of the presence of a malignancy.

Example 2

Detection of Epigenetic Changes in Inaccessible gDNA

DNA methylation is an epigenetic modification that inactivates genes by compacting the DNA and rendering it inaccessible to transcription factors and the transcriptional machinery. In most human cancers, specific tumor suppressor genes are silenced by aberrant DNA methylation. Such silencing is associated with a change in chromatin conformation from an open, accessible structure to a closed, inaccessible conformation. The present example illustrates the determination of a difference in the DNA methylation state of a tumor suppressor promoter in a subpopulation of inaccessible DNA, relative to the total DNA population in a mixture of DNA derived from cancerous and non-cancerous cells. This example demonstrates the use of the present methods to identify a small number of cancerous cells in a larger background of non-cancerous cells (e.g., as in a tissue biopsy).

The human glutathione S-transferase pi 1 ("GSTP1") gene promoter was analyzed. In non-cancerous prostate cells, GSTP1 is highly expressed, its promoter is not methylated and it is an accessible chromatin conformation. In contrast, in cancerous prostate cells GSTP1 is not expressed, its promoter is highly methylated and it is in an inaccessible chromatin configuration (Okino et al, Mol. Carcinog. (2007) 46:839-846). Two human cell lines were analyzed. HCT15 cells are derived from colon tissue and express GSTP1 similar to non-cancerous prostate tissue. LNCaP cells are a prostate cancer cell line that retain the cancerous GSTP1 expression characteristics.

Methods

In situ nuclease digestion was performed as described in (formerly co-pending, now abandoned) U.S. application Ser. No. 12/618,076, the entire content of which is incorporated herein by reference in its entirety for all purposes. Briefly, cells were treated when they reached 90% confluence. The culture media was aspirated and a permeabilization/digestion buffer was gently layered on the cells. For cells treated with MnlI the permeabilization/digestion buffer contained lysolecithin, NaCl, Tris-HCl, $MgCl_2$, DTT, BSA and MnlI. For cells treated with DNase I, the permeabilization/digestion buffer contained lysolecithin, Tris-HCl, $MgCl_2$, $CaCl_2$ and DNase I. The permeabilized cells were then incubated at 37° C. for 1 hour. Following incubation, lysis/stop solution (100 mM Tris-HCl pH 7.4, 100 mM NaCl, 100 mM EDTA, 5% N-lauroylsarcosine (w/v), 80 µg/ml RNase A and 3 mg/ml proteinase K) was added to the permeabilization/digestion buffer and the cell lysates were incubated at 37° C. for 10 minutes.

Genomic DNA was isolated from cultured cells by standard procedures. Completely methylated human DNA and completely unmethylated human DNA were purchased from Qiagen and used as controls. The DNA samples were either mock digested or digested with McrBC, HhaI or a combination of both enzymes as described, e.g., in Holemon et al, BioTechniques, (2007) 43:683-693). McrBC is a methylation-dependent nuclease that only digests methylated DNA; HhaI is a methylation-sensitive restriction enzyme that only digests DNA that is not methylated. Following enzyme treatment 5 ng of each DNA sample was amplified by real-time PCR using primers specific for the human GSTP1 promoter. The $\Delta Ct$ value comparing the mock digested sample with the enzyme digested samples are reported. Undigested DNA results in lower $\Delta Ct$ values; conversely, digested DNA results in higher $\Delta Ct$ values.

Results

Analysis of Total DNA

The completely methylated DNA sample was significantly digested with McrBC, but was not digested with HhaI ($\Delta Ct=5.0$ and $-0.5$ respectively). In contrast, the completely unmethylated DNA sample was not digested with McrBC, but was digested with HhaI ($\Delta Ct=-0.2$ and 4.8 respectively). In addition, no significant further digestion is detected in either DNA sample after treatment with both enzymes. These results are as expected and demonstrate that the present methods can readily distinguish methylated and unmethylated DNA samples. Analysis of total DNA from HCT15 cells revealed that it had a digestion profile similar to unmethylated DNA. In contrast, total DNA from LNCaP cells had a digestion profile consistent with methylated DNA (Table 1). These findings are consistent with results published in Okino, et al., supra, and indicate that the GSTP1 promoter in LNCaP cells is extensively methylated whereas it has little or no methylation in HCT15 cells.

TABLE 1

| DNA Sample | $\Delta Ct$ McrBc | $\Delta Ct$ HhaI | $\Delta Ct$ McrBC + Hha |
|---|---|---|---|
| Completely Methylated DNA | 5.0 | −0.5 | 5.6 |
| Completely Unmethylated DNA | −0.2 | 4.8 | 4.6 |
| Total HCT15 DNA | −0.3 | 9.5 | 8.4 |
| Total LNCaP DNA | 2.6 | −0.3 | 3.1 |

Analysis of Mixed DNA Samples Comparing Total DNA and Inaccessible DNA

HCT15 and LNCaP cells were treated with a nuclease in situ to digest accessible chromatin. The remaining DNA, which represents DNA that was originally in an inaccessible chromatin conformation, was then purified. To simulate a biopsy sample containing a small amount of cancerous cells in a background of non-cancerous cells, HCT15 and LNCaP DNA samples isolated from untreated cells (representative of total DNA) and nuclease treated cells (representative of inaccessible DNA) were mixed in either a 90:10 ratio or a 97:3 ratio. The mixed DNA samples were digested with McrBC and/or HhaI. The results (Table 2) demonstrate that the GSTP1 promoter in the mixed samples of total DNA was digested by HhaI. In addition, a low level of McrBC digestion was detected because GSTP1 digestion is more complete in the McrBC+HhaI samples than in the samples digested with HhaI alone. These findings indicate that the DNA methylation assay correctly identifies that the GSTP1 promoter is partially methylated in both DNA samples. In addition, because the extent of HhaI digestion is lower in the 90:10 sample than in the 97:3 sample ($\Delta Ct=2.5$ and 4.4, respectively) the DNA methylation assay has correctly determined that the extent of GSTP1 promoter methylation is higher in the 90:10 sample than in the 97:3 sample.

TABLE 2

| DNA Fraction | HCT15 | LNCaP | $\Delta Ct$ McrBC | $\Delta Ct$ HhaI | $\Delta Ct$ McrBC + Hha |
|---|---|---|---|---|---|
| Total | 90% | 10% | 0.0 | 2.5 | 6.1 |
| Inaccessible | 90% | 10% | 3.3 | 0.3 | 4.6 |

TABLE 2-continued

| DNA Fraction | HCT15 | LNCaP | ΔCt McrBC | ΔCt HhaI | ΔCt McrBC + Hha |
|---|---|---|---|---|---|
| Total | 97% | 3% | 0.0 | 4.4 | 8.1 |
| Inaccessible | 97% | 3% | 1.6 | 0.6 | 3.4 |

The GSTP1 promoter methylation results are much different in the samples where inaccessible DNA is assessed. In both the 90:10 and 97:3 samples, significant digestion with McrBC (ΔCt=3.3 and 1.6 respectively) and little digestion with HhaI (ΔCt=0.3 and 0.6 respectively) was observed. These findings reveal that the GSTP1 promoter in the inaccessible DNA subpopulation is highly methylated and, thus, significantly different than the total DNA population. These results indicate that comparison of target gene methylation in total DNA and inaccessible DNA can reveal distinct DNA methylation differences in a small subpopulation, and shows that cancerous cells at a 3% level can be detected in a tumor biopsy.

Example 3

Detection of Epigenetic Changes Between Two Alleles

Genomic imprinting is an epigenetic process that inactivates one chromosomal allele by DNA methylation and chromatin compaction. The other allele is maintained in an accessible chromatin structure and is transcriptionally active resulting in monoallelic gene expression. Genomic imprinting occurs in a parent-of-origin specific fashion. Proper imprinting is important for normal development, and imprinting defects are associated with numerous genetic diseases and syndromes.

To detect imprinted genes, cells are split into two portions. The first portion is treated with a nuclease in situ to digest accessible chromatin. The second portion is not treated with a nuclease. gDNA isolated from the first portion of cells represents the subpopulation of gDNA that is in an inaccessible chromatin structure. gDNA isolated from the second cell portion represents total gDNA.

Assessment of the two gDNA samples for DNA methylation at imprinted gene regions can indicate important facets of the imprinting status. For genes that are properly imprinted it is expected that complete DNA methylation of the candidate genomic region is observed in the gDNA sample representing inaccessible DNA. However, only partial (50%) candidate region DNA methylation is expected when the total gDNA sample is analyzed. For samples that have imprinting defects, deviation from the expected DNA methylation profile is detected.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of testing for DNA methylation differences in one or more genomic DNA regions of different cells in a biopsy sample, wherein the biopsy sample comprises a large background of non-cancerous cells, the method comprising:

a) dividing the biopsy sample comprising the cells, which comprise genomic DNA (gDNA), into at least a first portion comprising a first portion of the cells and a second portion comprising a second portion of the cells;

b) permeabilizing the cells in the first portion, thereby producing permeabilized cells;

c) treating the permeabilized cells of the first portion with a nuclease to digest gDNA that is accessible to the nuclease in the permeabilized cells and leave intact gDNA that is inaccessible to the nuclease in the permeabilized cells, thereby producing a first portion that is enriched in inaccessible gDNA;

d) purifying gDNA from the first portion that is enriched in inaccessible gDNA, thereby producing enriched gDNA of the first portion, and purifying gDNA from the second portion, thereby producing total gDNA of the second portion;

e) analyzing DNA methylation in the one or more gDNA regions in the enriched gDNA of the first portion and DNA methylation in the same one or more gDNA regions in the total gDNA of the second portion; and f) determining whether the DNA methylation in the one or more gDNA regions in the enriched gDNA of the first portion is different from the DNA methylation in the same one or more gDNA regions in the total gDNA of the second portion, wherein:

the presence of DNA methylation differences between the one or more gDNA regions in the enriched gDNA of the first portion and the same one or more gDNA regions in the total gDNA of the second portion indicates the presence of DNA methylation differences in the one or more gDNA regions of the cells in the biopsy sample; and the absence of DNA methylation differences between the one or more gDNA regions in the enriched gDNA of the first portion and the same one or more gPNA regions in the total gPNA of the second portion indicates the absence of DNA methylation differences in the one or more DNA regions of the cells in the biopsy sample.

2. The method of claim 1, wherein steps b) and c) are performed in a single buffer.

3. The method of claim 1, wherein the biopsy sample is a solid tissue sample.

4. The method of claim 1, wherein the nuclease comprises a restriction endonuclease.

5. The method of claim 1, wherein the DNA methylation in the one or more gDNA regions in the enriched gDNA of the first portion and the DNA methylation in the same one or more gDNA regions in the total gDNA of the second portion are determined using a methylation-sensitive restriction enzyme (MSRE) or a methylation-dependent restriction enzyme (MDRE).

6. The method of claim 1, wherein the DNA methylation in the one or more gDNA regions in the enriched gDNA of the first portion and the DNA methylation in the same one or more gDNA regions in the total gDNA of the second portion is determined by a method comprising separately contacting the enriched gDNA of the first portion and the total gDNA of the second portion with bisulfite.

7. The method of claim 1, wherein the DNA methylation in the one or more gDNA regions in the enriched gDNA of the first portion and the DNA methylation in the same one or more gDNA regions in the total gDNA of the second portion is determined by:

(i) a method comprising an affinity purification step using a protein that binds with high affinity to methylated DNA, or (ii) a method comprising direct sequencing of the one or more gDNA regions in the enriched gDNA of the first portion and the same one or more gDNA regions in the total gDNA of the second portion using single-molecule real-time sequencing or single-molecule nanopore DNA sequencing.

8. The method of claim 1, wherein the one or more gDNA regions comprise one or more regions of a promoter of a tumor suppressor gene.

9. The method of claim 1, wherein the nuclease comprises a DNase.

* * * * *